United States Patent
Eaton-Evans et al.

(10) Patent No.: US 12,053,233 B2
(45) Date of Patent: Aug. 6, 2024

(54) ABLATION PROBE

(71) Applicant: NATIONAL UNIVERSITY OF IRELAND, GALWAY, Galway (IE)

(72) Inventors: Jimmy Eaton-Evans, Galway (IE); Giuseppe Ruvio, Galway (IE); Jonathan Bouchier-Hayes, Galway (IE); Martin O'Halloran, Galway (IE); Mark Bruzzi, Galway (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 843 days.

(21) Appl. No.: 16/499,401

(22) PCT Filed: Mar. 29, 2018

(86) PCT No.: PCT/EP2018/058252
§ 371 (c)(1),
(2) Date: Sep. 30, 2019

(87) PCT Pub. No.: WO2018/178317
PCT Pub. Date: Oct. 4, 2018

(65) Prior Publication Data
US 2021/0161586 A1 Jun. 3, 2021

(30) Foreign Application Priority Data

Mar. 31, 2017 (EP) .................................... 17164403

(51) Int. Cl.
*A61B 18/14* (2006.01)
*A61B 1/00* (2006.01)
(Continued)

(52) U.S. Cl.
CPC ...... *A61B 18/1477* (2013.01); *A61B 1/00087* (2013.01); *A61B 1/018* (2013.01);
(Continued)

(58) Field of Classification Search
None
See application file for complete search history.

(56) References Cited

U.S. PATENT DOCUMENTS

| 3,668,573 A | 6/1972 | Martin |
| 4,366,457 A | 12/1982 | Bode et al. |

(Continued)

FOREIGN PATENT DOCUMENTS

| EP | 2508145 A1 | 10/2012 |
| EP | 3278755 A1 | 2/2018 |

(Continued)

OTHER PUBLICATIONS

Office Action issued for Japanese Patent Application No. JP2019-554411 on Feb. 22, 2022, 10 pages.
(Continued)

*Primary Examiner* — Ronald Hupczey, Jr.
(74) *Attorney, Agent, or Firm* — Husch Blackwell LLP

(57) ABSTRACT

An ablation probe (100; 200) suitable for insertion through the working channel of an intraluminal delivery device comprises an applicator (102; 202) arranged to apply radiation to heat surrounding tissue. The probe also comprises a feeding cable (104; 204) arranged to supply electromagnetic energy to the applicator (102; 202). The probe further comprises a first coolant flow path (106). There is also a deformable member (110; 210) arranged to move between an insertion configuration in which insertion of the probe is facilitated and a deployed configuration. A second coolant path (108), via which coolant is able to flow, is provided by the deformable member (110; 210) when in the deployed configuration. The probe further comprises a tube arranged to house a distal portion of the feeding cable, and the deformable member surrounds at least part of the tube, and the tube is formed from an elastic material.

19 Claims, 16 Drawing Sheets

(51) Int. Cl.
  *A61B 1/018* (2006.01)
  *A61B 1/267* (2006.01)
  *A61B 17/00* (2006.01)
  *A61B 18/00* (2006.01)
  *A61B 18/18* (2006.01)

(52) U.S. Cl.
  CPC ........ *A61B 1/2676* (2013.01); *A61B 18/1492* (2013.01); *A61B 18/1815* (2013.01); *A61B 2017/00477* (2013.01); *A61B 2017/00862* (2013.01); *A61B 2017/00867* (2013.01); *A61B 2018/00023* (2013.01); *A61B 2018/00077* (2013.01); *A61B 2018/00083* (2013.01); *A61B 2018/00285* (2013.01); *A61B 2018/00577* (2013.01); *A61B 2018/00791* (2013.01); *A61B 2018/00875* (2013.01); *A61B 2018/00982* (2013.01); *A61B 2018/1861* (2013.01); *A61B 2018/1869* (2013.01)

(56) References Cited

U.S. PATENT DOCUMENTS

| | | | |
|---|---|---|---|
| 4,967,765 A | | 11/1990 | Turner et al. |
| 5,275,597 A | | 1/1994 | Higgins et al. |
| 5,755,465 A | | 5/1998 | Stewart, Jr. et al. |
| 9,173,706 B2 | | 11/2015 | Rossetto |
| 2005/0015081 A1 | * | 1/2005 | Turovskiy .............. A61B 18/18 607/156 |
| 2005/0165389 A1 | | 7/2005 | Swain et al. |
| 2005/0245920 A1 | * | 11/2005 | Vitullo .................. A61B 18/18 607/156 |
| 2008/0051776 A1 | * | 2/2008 | Bliweis ................. A61B 18/02 606/21 |
| 2008/0135288 A1 | | 6/2008 | Taylor et al. |
| 2010/0076299 A1 | * | 3/2010 | Gustus ................. A61B 18/245 601/3 |
| 2011/0180323 A1 | | 7/2011 | Luzzi |
| 2012/0143180 A1 | | 6/2012 | Lee, Jr. et al. |
| 2012/0259326 A1 | * | 10/2012 | Brannan ............. A61B 18/1815 606/33 |
| 2013/0178841 A1 | * | 7/2013 | Reid, Jr. ............ A61B 18/1815 606/46 |
| 2013/0345699 A1 | | 12/2013 | Brannan et al. |
| 2014/0128862 A1 | | 5/2014 | Rossetto et al. |
| 2014/0276739 A1 | | 9/2014 | Brannan et al. |
| 2017/0273737 A1 | | 9/2017 | Iwanami et al. |
| 2018/0036081 A1 | | 2/2018 | Dickhans et al. |

FOREIGN PATENT DOCUMENTS

| | | | | |
|---|---|---|---|---|
| JP | H3-57174 A | | 3/1993 | |
| JP | 2004187703 A | | 7/2004 | |
| JP | 2012187405 A | | 10/2012 | |
| JP | 2014516616 A | | 7/2014 | |
| JP | 2015509390 A | | 3/2015 | |
| WO | 2009098513 A1 | | 8/2009 | |
| WO | 2009137819 A1 | | 11/2009 | |
| WO | WO-2009137819 A1 | * | 11/2009 | ......... A61B 18/1206 |
| WO | 2011140087 A2 | | 11/2011 | |
| WO | 2017067910 A2 | | 4/2017 | |

OTHER PUBLICATIONS

International Search Report and Written Opinion for International Application No. PCT/EP2018/058252 dated Jun. 25, 2018, 12 pages.
International Search Report and Written Opinion for International Application No. PCT/EP2019/058072 dated Jul. 8, 2019, 16 pages.
Extended European Search Report for EP Application No. 17164403 dated Sep. 13, 2017, 9 pages.
Extended European Search Report for EP Application No. 18197568.1 dated May 2, 2019, 8 pages.

* cited by examiner

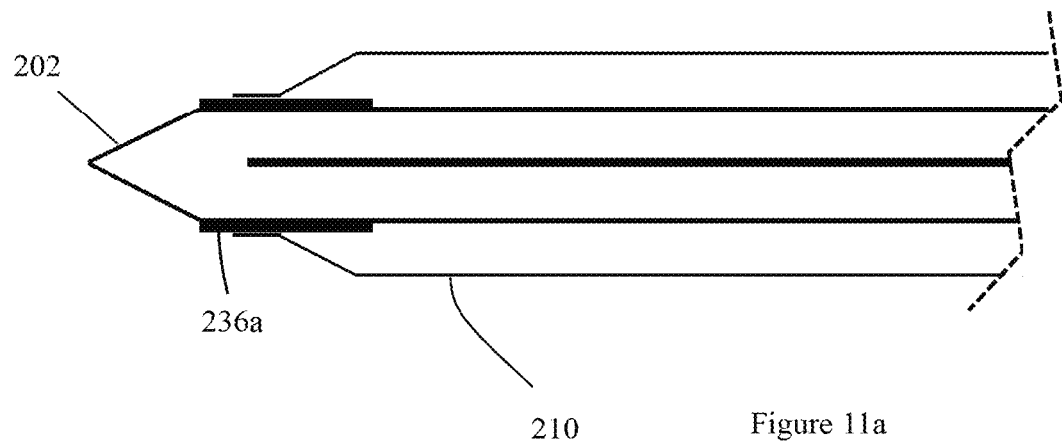
Figure 11a
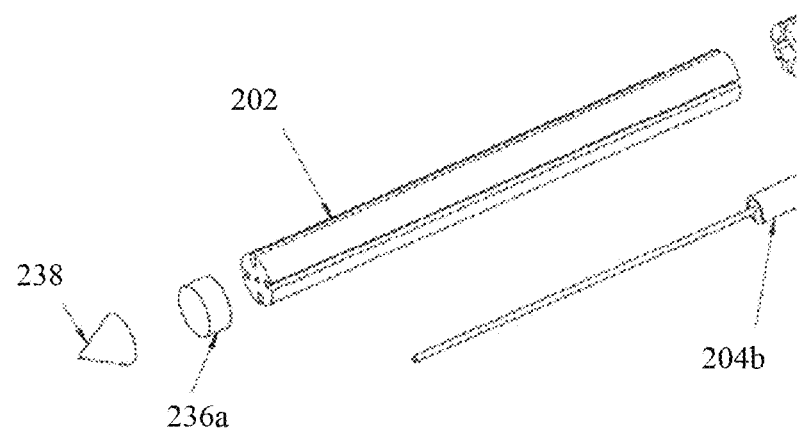
Figure 11b
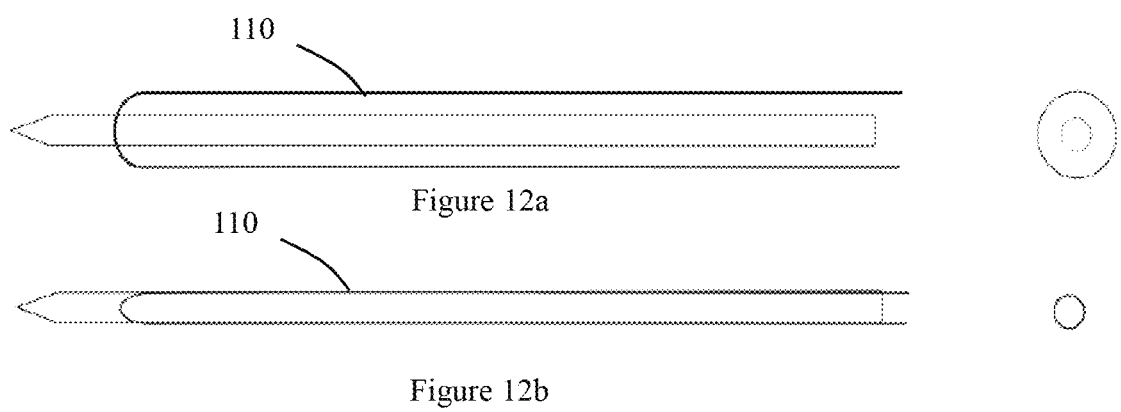
Figure 12a
Figure 12b

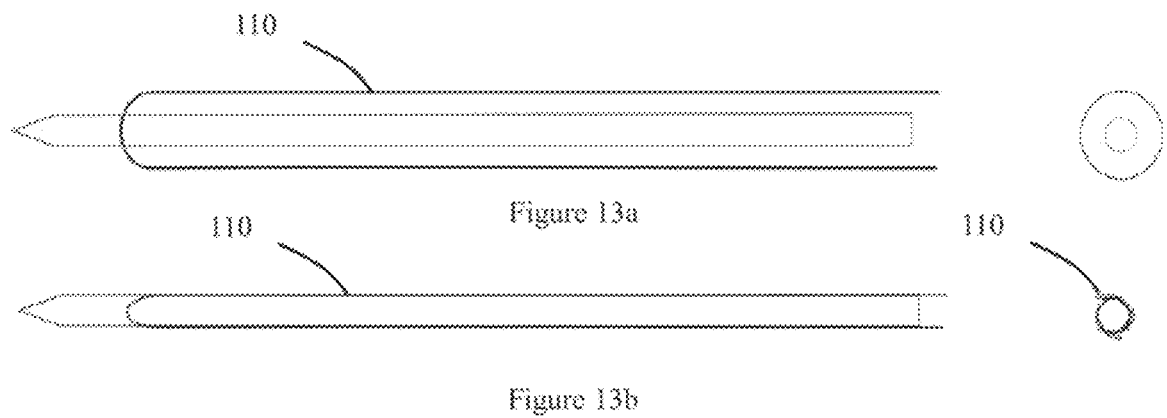
Figure 13a
Figure 13b
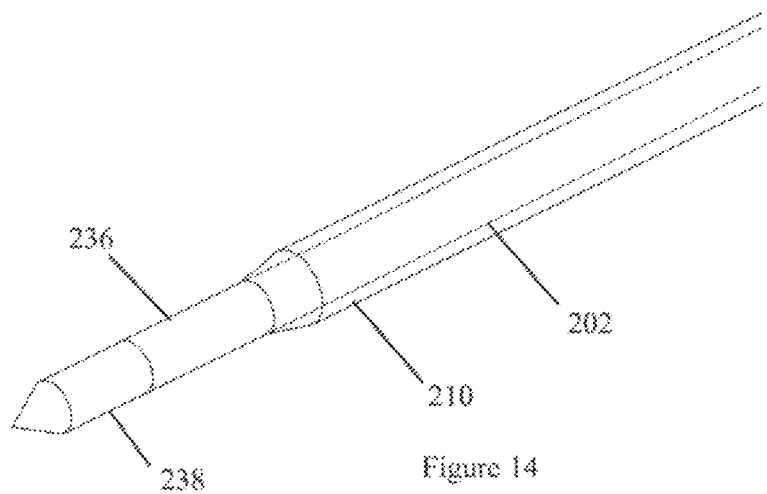
Figure 14

ABLATION PROBE

This application relates to an ablation probe. In particular, this application relates to an ablation probe that may be used to generate heat within tissue to destroy tissue growths.

Thermal ablation can be used to destroy tissue growths within the body which can be malignant. Current ablation systems use applicators that deliver Radio Frequency (RF) energy (or microwave energy) to the tissue surrounding the applicator tip. This causes localised heating and destruction of the malignant cells. These applicators may be designed for percutaneous delivery and are therefore relatively short in length and large in diameter. However, many disease locations cannot be safely or easily accessed percutaneously. For example, the location of the pancreas behind the liver makes it difficult to access percutaneously. Similarly, access to the lung through the chest wall can cause a pneumothorax. Large diameter applicators may also cause undesired tissue damage during insertion. This limits the range of indications where thermal ablation therapy can be successfully delivered using existing percutaneous applicators.

An endoscope can be used to access a number of disease locations that border the gastrointestinal tract. These include the pancreas, biliary tree, lymph nodes and a number of significant blood vessels. Furthermore, Endoscopic Ultrasound (EUS) systems provide a means of identifying lesions in tissue adjacent to the gastrointestinal tract using an ultrasound imaging system that is integrated within the endoscope. A biopsy needle can be delivered through the EUS system and directed to the target site under ultrasound guidance. Similar endoscopes are available to assess disease locations in the lung using both ultrasound and navigation systems. This technology can be used to guide an extended working channel or steerable catheter to the disease location. Known applicator designs are not particularly suited for delivery through the working channel of an endoscope or lung navigation system, as they are typically too large in cross section and are of insufficient length and flexibility.

There are significant challenges associated with miniaturising and extending the length of ablation applicators (particularly microwave applicators) to make them suitable for endoscope delivery. Smaller devices can carry less power due to electrical losses in the power cable used to supply energy to the applicator tip. Electrical losses reduce power that reaches the applicator tip, meaning less heat is generated at the tip and the therapy takes longer to deliver. These losses are manifested as heat along the length of the cable and must be controlled using a cooling system to prevent damage to the cable or endoscope, or injury to the patient. To maintain cooling along the length of a narrow cable, a high pressure cooling fluid is required. Known dedicated conduits provided for coolant flow increase the overall cross-section of the ablation probe and reduce flexibility making it unsuitable for endoscopic use. Furthermore, the applicator must have a minimal profile and favourable mechanical properties to pierce into the organ and reach the target lesion.

In one aspect, the present application provides an ablation probe suitable for insertion through the working channel of an intraluminal delivery device, comprising:
  an applicator arranged to apply radiation to heat surrounding tissue;
  a feeding cable arranged to supply electromagnetic energy to the applicator;
  a first coolant flow path via which coolant is able to flow; and
  a deformable member arranged to move between an insertion configuration in which insertion of the probe is facilitated and a deployed configuration,
  wherein a second coolant path, via which coolant is able to flow, is provided by the deformable member when in the deployed configuration.
  wherein the ablation probe further comprises:
    a tube arranged to house a distal portion of the feeding cable, and wherein the deformable member surrounds at least part of the tube, and wherein the tube is formed from an elastic material.

By providing a tube formed from an elastic material the ablation probe may withstand permanent deformation after being delivered through a working channel along a tortuous path through patient anatomy. This may avoid the ablation probe following a curved unpredictable path after leaving the working channel and allow it to be more easily delivered to the required ablation site.

In another aspect, the present application provides an ablation probe, comprising: an applicator arranged to apply radiation to heat surrounding tissue; a feeding cable arranged to supply electromagnetic energy to the applicator; a first coolant flow path via which coolant is able to flow; and a deformable member arranged to move between an insertion configuration in which insertion of the probe is facilitated and a deployed configuration, wherein a second coolant path, via which coolant is able to flow, is provided by the deformable member when in the deployed configuration.

When the deformable member is in the insertion configuration, the ablation probe may have a profile suitable to aid insertion. This may be a small and compact profile, or a suitable shape or geometry. In the insertion configuration, the ablation probe may be inserted into tissue while reducing undesired tissue injury. The insertion profile may also aid delivery of the ablation probe via an endoscope or lung navigation system. Once in the desired position, the deformable member may be moved to the deployed configuration to provide a return coolant path. The ablation probe may therefore have a small profile during insertion when cooling is not required. Once in position, the deformable member may be deployed to then provide cooling during use of the ablation probe.

Optionally, the tube may be formed from a superelastic material. For example a metal alloy (e.g. NiTi known as Nitinol) that can elastically recover large strains (e.g. 5%). Optionally the tube may be at least partially formed from an electrically conductive material.

Any of the following statements may be used in combination with the first aspect or the second aspect where appropriate, and may be used in any combination with each other.

Optionally, the second coolant path is provided only by the deformable member along at least a portion of a length of the probe.

Optionally, the deformable member is fluidly connected to a distal end of the first coolant path.

Optionally, a distal portion of the feeding cable has a distal cross sectional size, and a proximal portion of the feeding cable has a proximal cross sectional size, wherein the distal cross sectional size is less than the proximal cross sectional size.

Optionally, the probe comprises: a) needle portion comprising the deformable member, the applicator, the distal portion of the feeding cable and a distal portion of the first coolant path; and b) a catheter portion comprising a proximal portion of the feeding cable, the proximal portion of the first coolant path, and a (preferably non-deformable) coolant conduit, wherein the deformable member is fluidly connected to the non-deformable coolant conduit at a boundary between the needle portion and the catheter portion.

Optionally, a greatest cross sectional size of the needle portion may be less than a greatest cross sectional size of the catheter portion. This may allow the needle portion to access an ablation site whilst reducing any potential for tissue damage.

Optionally a distal portion of the feeding cable may have a distal cross sectional size, and the proximal portion of the feeding cable has a proximal cross sectional size, wherein the distal cross sectional size is less than the proximal cross sectional size.

The combination of the needle portion and the catheter portion of the ablation probe provides an advantageous balance between delivering a suitable level of electromagnetic energy to the applicator along the length of the working channel, while ensuring minimally invasive access to the ablation site. By providing a needle portion having a relatively small cross section feeding cable, and a deployable deformable member to provide cooling, the overall cross section in that portion of the device can be reduced. Damage to tissue can therefore be reduced when positioning the applicator to perform the ablation procedure. The catheter portion having a relatively larger thickness feeding cable provides a suitable delivery of energy to the applicator. The catheter portion is therefore optimised for energy delivery over the long length of a working channel, while the needle portion is optimised for minimally invasive access to the ablation site.

Optionally, the ablation probe may further comprise a connector arranged to mechanically and electrically splice the distal portion of the feeding cable to the proximal portion of the feeding cable.

Optionally, the connector may comprise a joining member arranged to mechanically and electrically couple the distal portion of the feeding cable to the proximal portion of the feeding cable, wherein the joining member comprises a proximal end shaped to receive the proximal portion of the feeding cable and a distal end shaped to receive the distal portion of the feeding cable. This may allow a secure, compact mechanical and electrical coupling to be provided between the different portions of the feeding cable.

Optionally, a portion of the connector may be arranged to extend within the tube housing the distal portion of the feeding cable to form a mechanical coupling between them. This may reinforce the joint between the connector and the distal portion of the feeding cable.

Optionally, the connector may comprise a dielectric member, wherein the dielectric member is arranged to at least partly fill a region between an inner conductor of the proximal and/or distal portion of the feeding cable and a the respective outer conductor of the proximal and/or distal portion of the feeding cable. The dielectric member may facilitate heat transfer from the inner conductor.

Optionally, the connector may comprise a sealing member, sealing member at least partially surrounding a connection region between the connector and either or both of the distal portion of the feeding cable and the proximal portion of the feeding cable. The sealing member may provide a waterproof seal to reduce the risk of coolant ingress (for example water ingress) into the joint between the portions of the feeding cable.

Optionally, the catheter coolant conduit may be formed from a catheter tube coupled to the deformable member, and wherein the applicator, the tube housing the distal portion of the feeding cable and the feeding cable are movable relative to the catheter tube between a sheathed configuration in which a distal tip of the applicator is surrounded by the deformable member and an unsheathed position in which the distal tip of the applicator is not surrounded by the deformable member.

Optionally, wherein in the sheathed configuration the applicator distal tip is located within the catheter tube wherein in the unsheathed configuration the distal tip of the applicator is not located within the catheter tube. The applicator and feed cable can move relative to the catheter tube to move the applicator tip and deformable member in and out of the catheter tube.

Optionally, the deformable member is arranged to at least partly surround the applicator in the deployed configuration. This may reduce the need for dedicated cooling channels in the applicator which may be difficult to manufacture and may reduce applicator performance.

Optionally, when in the deployed configuration, the deformable member is shaped to anchor the ablation probe relative to the surrounding tissue.

Optionally, the ablation probe may further comprise a bridging member arranged to couple the applicator to the tube housing the distal portion of the feeding cable, wherein the bridging member comprises a bridging tube surrounding a part of the tube and a part of the applicator so that it bridges the connection between them.

Optionally, a tight fit is provided between the bridging tube and each of the tube and applicator so as to form a friction fit between them.

Optionally, the deformable member comprises one or more elongate deformable channels running along the length of the ablation probe.

Optionally, the one or more deformable channels comprise a plurality of channels equally spaced around a circumference of the ablation probe.

Optionally, the deformable member is arranged to expand to a maximum threshold size in the deployed configuration.

Optionally, the deformable member comprises: a) a compliant or semi-compliant material arranged to expand or contract in size in order to move between the insertion and deployed configurations; and/or b) a non-compliant material arranged to fold or unfold in order to move between the insertion and deployed configurations.

Optionally, the ablation probe further comprises a coupling member, the coupling member arranged to couple the deformable member to the applicator.

Optionally, the coupling member may be formed from a material different from the applicator, wherein the coupling member is arranged to form a bonding site to which the deformable member is bonded. By forming the coupling member from a different material to the applicator a more suitable material for bonding to the deformable member may be used. It may, for example, be formed from the same material from the deformable member to aid bonding.

Optionally the coupling member may be shaped to form a mechanical coupling with the applicator. Preferably the coupling member may be formed from a coupling tube surrounding the applicator, the coupling tube having a close fit with an outer surface of the applicator to form a friction fit between them. This may allow a secure coupling between the deformable member and the applicator without bonding directly to the applicator.

Optionally, the coupling member may be formed from an electrically insulating material.

Optionally, the first coolant path comprises a coolant channel formed between an inside surface of a or the tube surrounding the feeding cable and an outside surface of the feeding cable.

Optionally, the first coolant path comprises one or more coolant channels formed in the body of a or the tube housing the feeding cable.

Optionally, the feeding cable comprises an inner conductor arranged to transmit a signal to the applicator, the inner conductor being surrounded by an insulating material, and an outer conductor arranged to shield the inner conductor, and wherein the first coolant path comprises one or more coolant channels formed in the outer conductor.

Optionally, the one or more coolant channels comprise one or more slots in an outer surface of the tube or an outer surface of the outer conductor and wherein the ablation probe further comprises a membrane disposed around the tube or the outer conductor, the membrane arranged to separate the first coolant path and from the second coolant path.

Optionally, the one or more coolant channels are disposed along a length of the outer conductor or along a length of the tube surrounding the feeding cable.

Optionally, the one or more coolant channels comprise a plurality of channels spaced equally around a circumference of the outer conductor or tube surrounding the feeding cable.

Optionally, the plurality of channels comprises four channels spaced equally around the circumference of the outer conductor or the tube.

Optionally, the applicator further comprises one or more applicator coolant channels fluidly connected to the first coolant path.

Optionally, the one or more applicator coolant channels may be formed by one or more recesses in an outer surface of the body of the applicator. This may help facilitate cooling of the applicator.

Optionally, the deformable member may at least partly surround the applicator, and wherein the ablation probe may further comprise an insulating member disposed between the deformable member and the applicator. This may help to protect the deformable member from high temperatures produced by the applicator.

Optionally, the applicator may comprise an insertion region arranged to extend into a or the tube housing the distal portion of the feeding cable, the insertion region may comprise one or more channels arranged to fluidly couple the first coolant path to the applicator coolant channels. This may provide a secure and compact coupling of the applicator and allow a supply of coolant to flow to the applicator coolant channels.

Optionally, ablation probe further comprises a sensor arranged to sense whether the deformable member has moved into the deployed configuration.

Optionally, the sensor is arranged to sense one or more properties of the applicator or the energy applied to the surrounding tissue to determine the configuration of the deformable member.

Optionally, the one or more sensors are provided within the deformable member.

Optionally, the one or more sensors comprise one or more temperature sensors and/or one or more impedance sensors.

Optionally, the probe further comprises a choke element disposed at a proximal end of the applicator.

Optionally, the choke element is formed from a mixture of a ceramic and a metallic material and coolant.

Optionally, the choke element is cooled by the coolant flowing via the first coolant path. Optionally, the choke element is integrated with a tube housing the feeding cable.

Optionally, the choke element comprises a portion of the applicator extending between the outer conductor of the feeding cable and a tube housing the feeding cable and preferably extending a distance equivalent to one quarter of a wavelength of the radiation applied by the applicator, and where the applicator material located within the tube is metallised to provide an electrical connection between the feed cable and the metal tube, thereby creating a metallic pocket and therefore a choke. Where there are channels in the section of applicator located in the metal tube to allow coolant flow through the choke that has been formed.

Optionally, the deformable member may be a second deformable member, the ablation probe may further comprise a first deformable member arranged to move between an insertion configuration in which insertion of the probe is facilitated and a deployed configuration, wherein the first coolant path is provided at least partly by the first deformable member when in the deployed configuration. This may provide additional space for coolant flow.

Optionally, the first deformable member may at least partly surround either or both of: a tube housing the distal portion of the feeding cable tube; and at least part of the applicator.

Optionally, the first coolant flow path may be formed by either or both of: a conduit formed between the distal portion of the feeding cable and the tube: and a conduit formed between the tube and the first deformable member.

Optionally, the needle portion may comprise a pointed tip adapted to pierce tissue during use.

Optionally, the needle portion may further comprise a sheath member, the sheath member being arranged to move between a first position in which it surrounds the pointed tip and a second position in which the pointed tip is uncovered.

Optionally, the intraluminal delivery device is one of an endoscope, a bronchoscope or a lung navigation system.

Embodiments of the invention will now be described, by way of example only, with reference to the accompanying drawings, in which.

Figure 2:
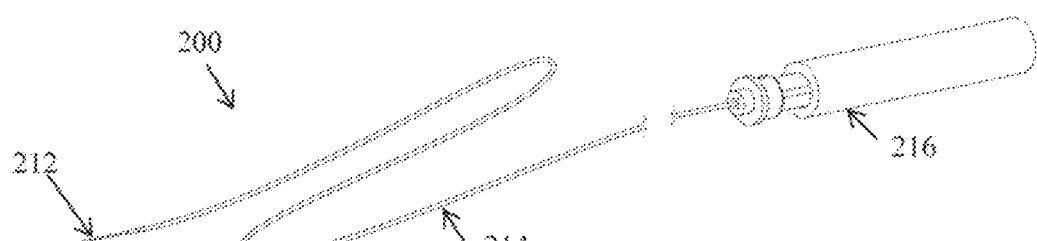
FIG. 2 shows a perspective view of an ablation probe according to an embodiment.
Figures 5A, 5B, 5C:
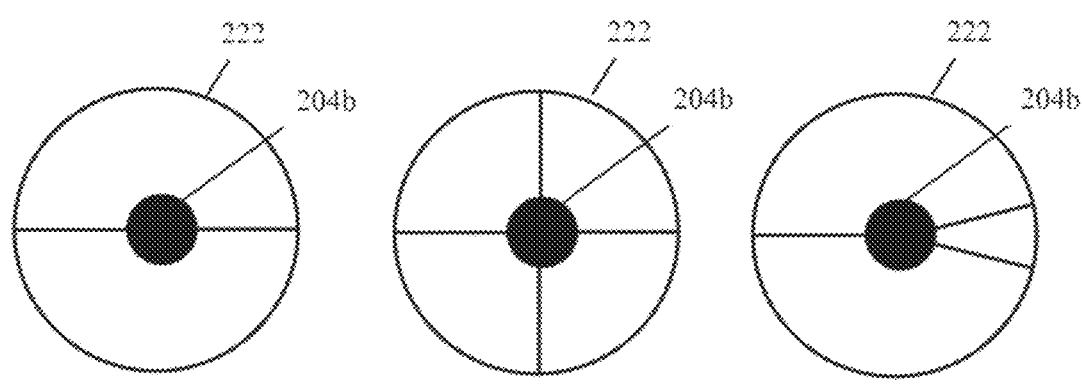
Figure 6A:
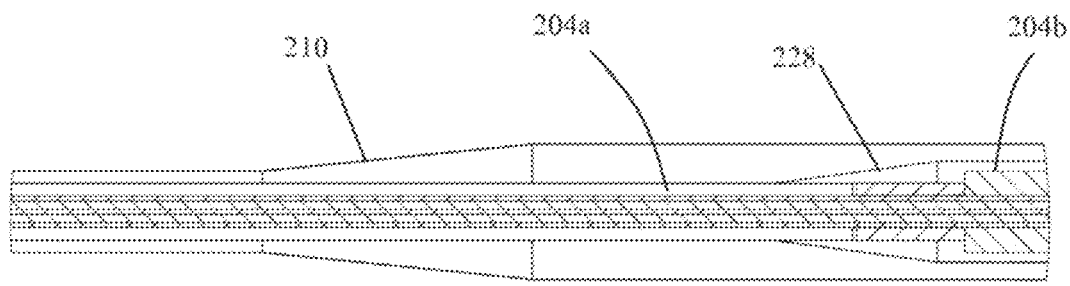
Figure 6B:
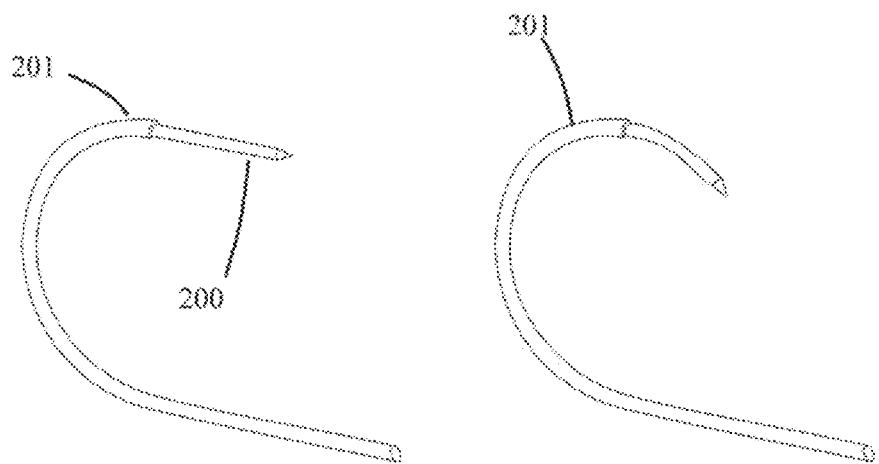
Figure 6C:
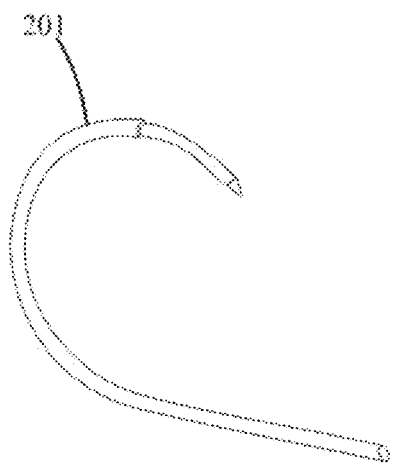
Figure 7:
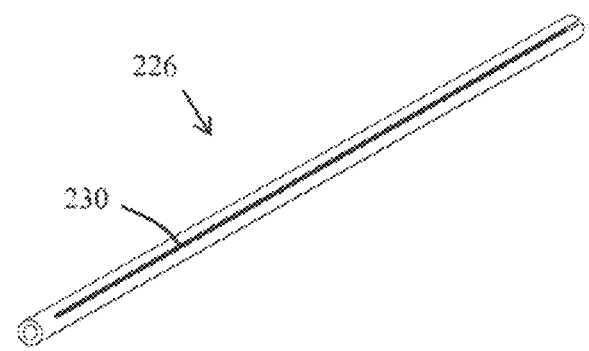
Figure 8A:
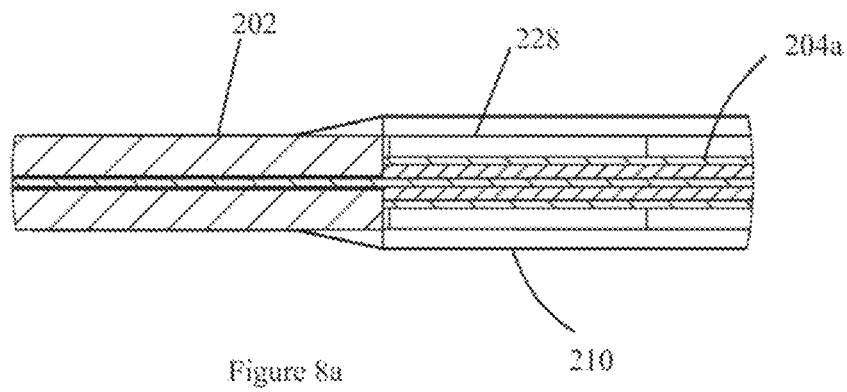
Figure 8B:
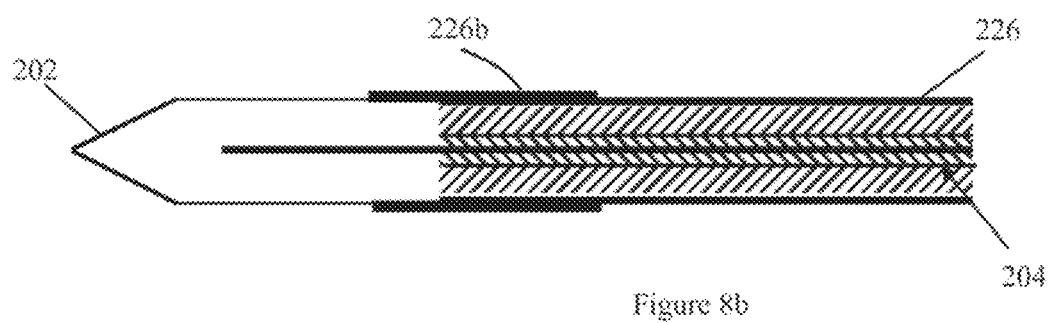
Figure 9:
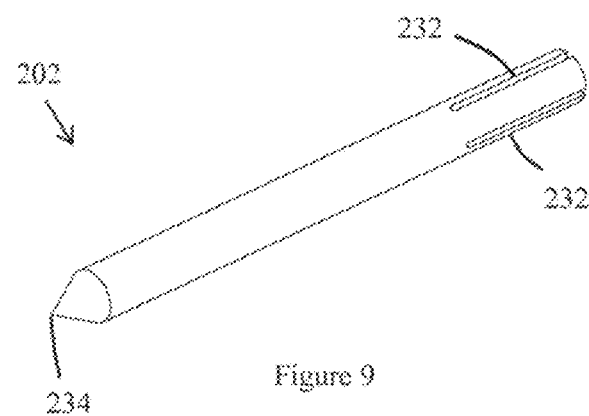
Figure 10A:
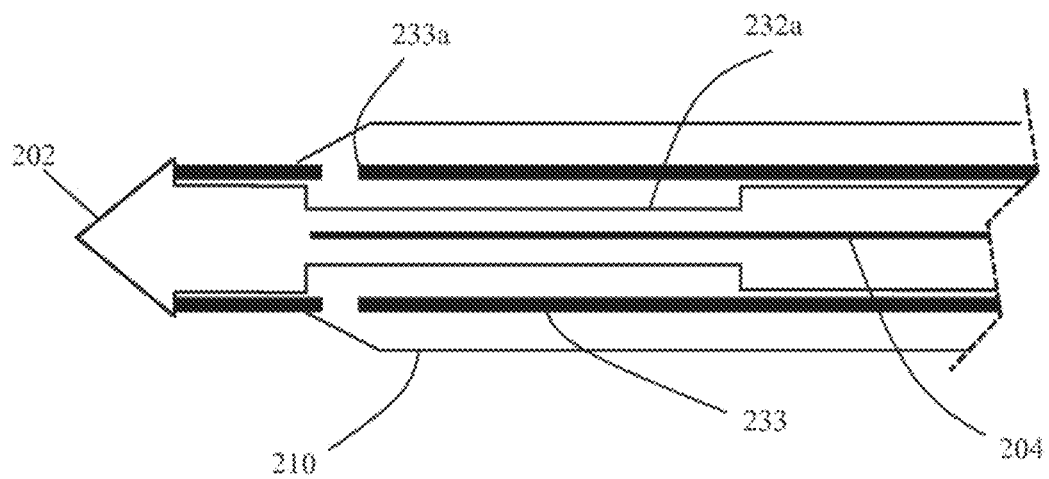
Figure 10B:
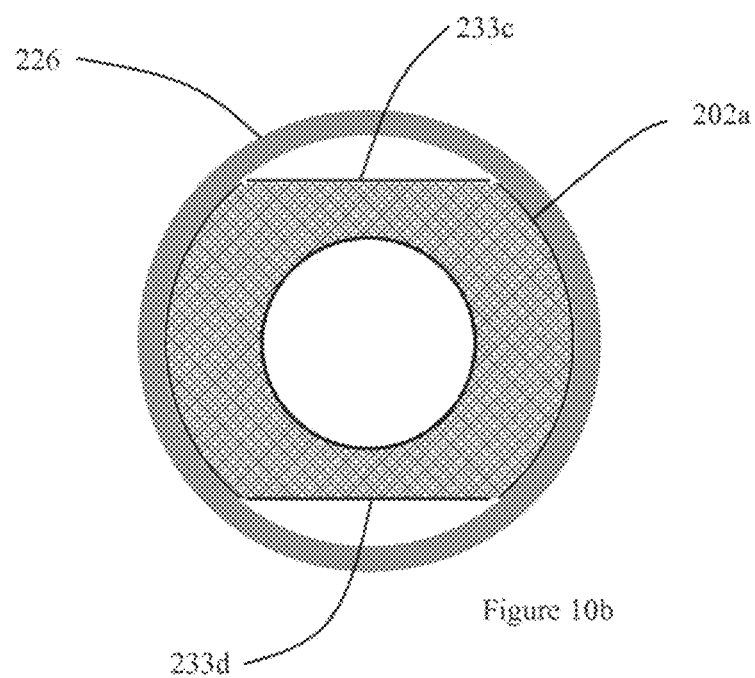
Figure 15:
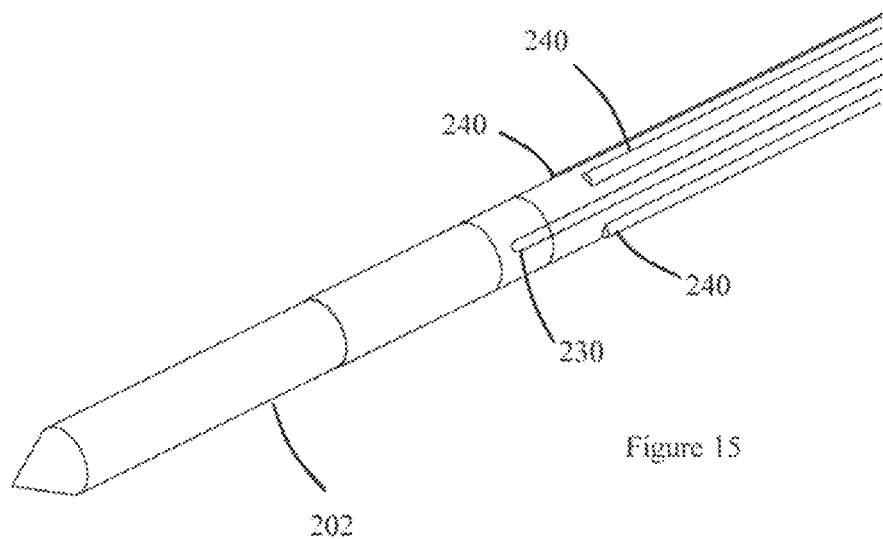
Figure 16:
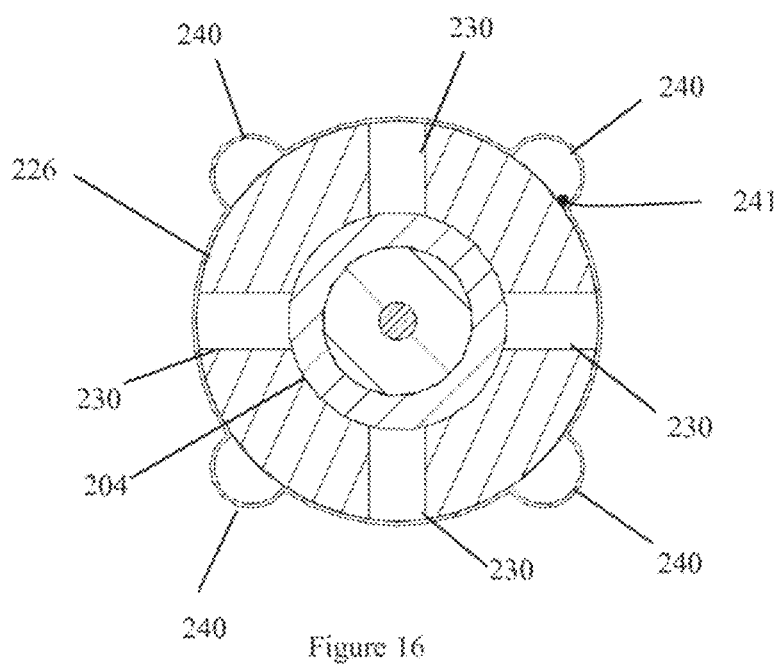
Figure 17:
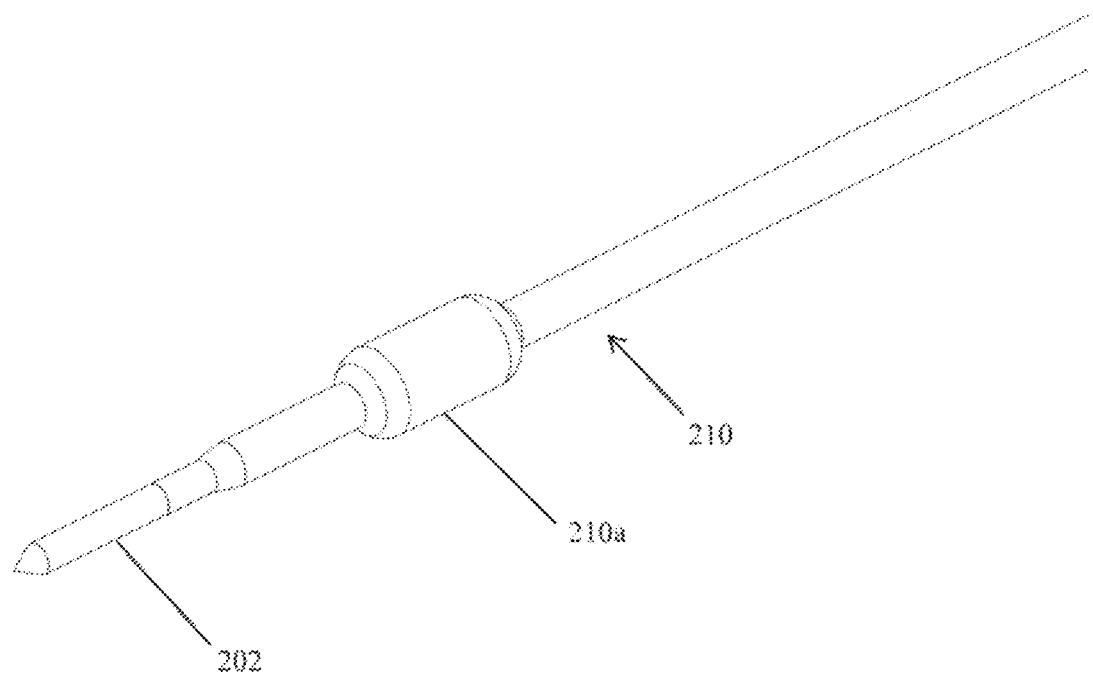
Figure 18A:
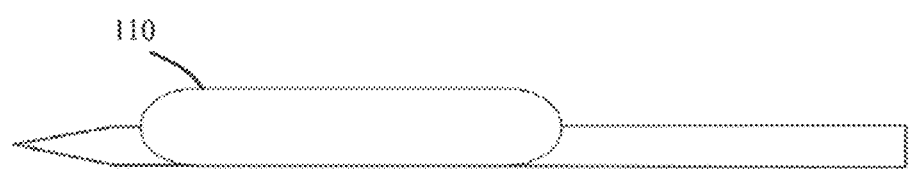
Figure 18B:
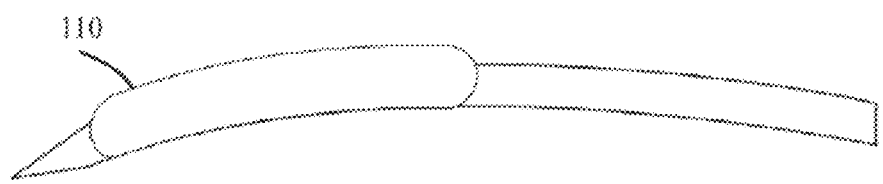
Figure 19:
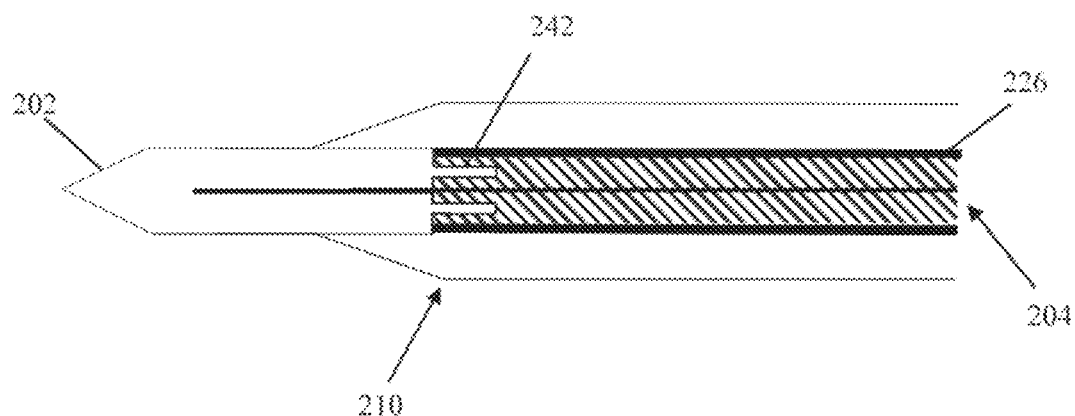
Figure 20:
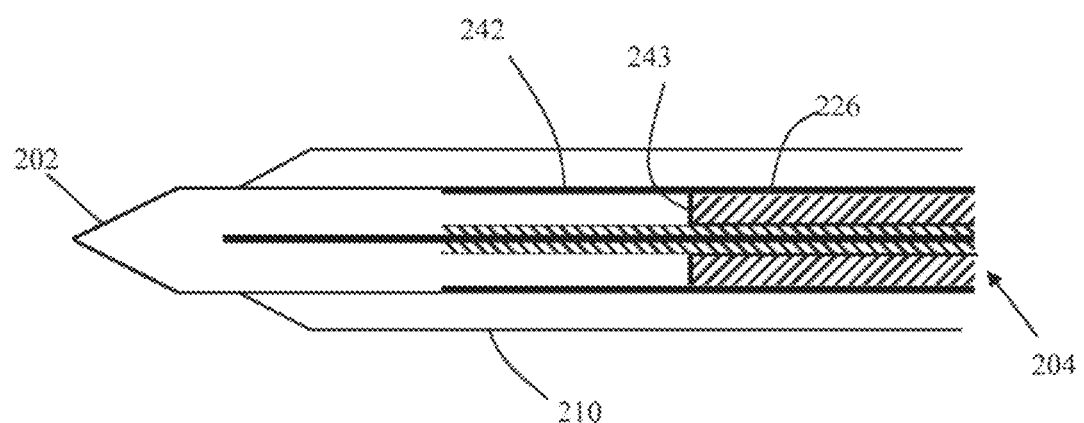
Figure 21:
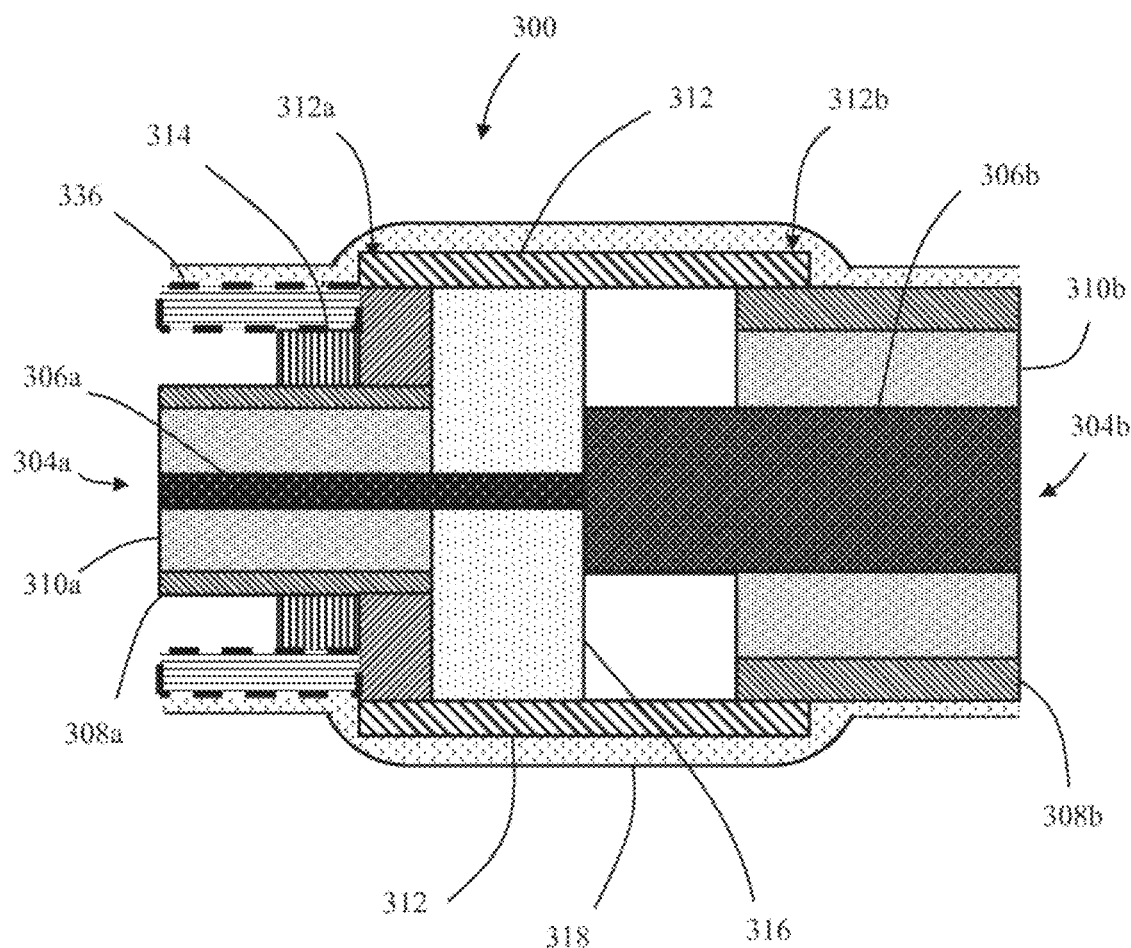
Figure 22A:
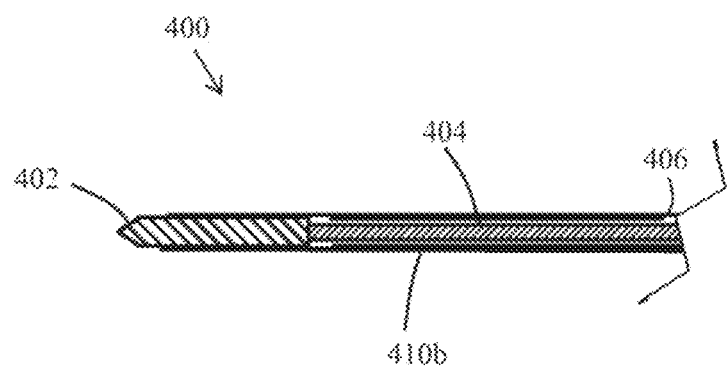
Figure 22B:
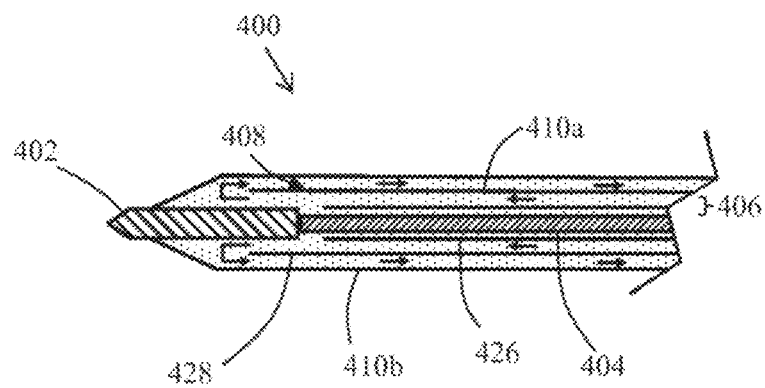
Figure 23A:
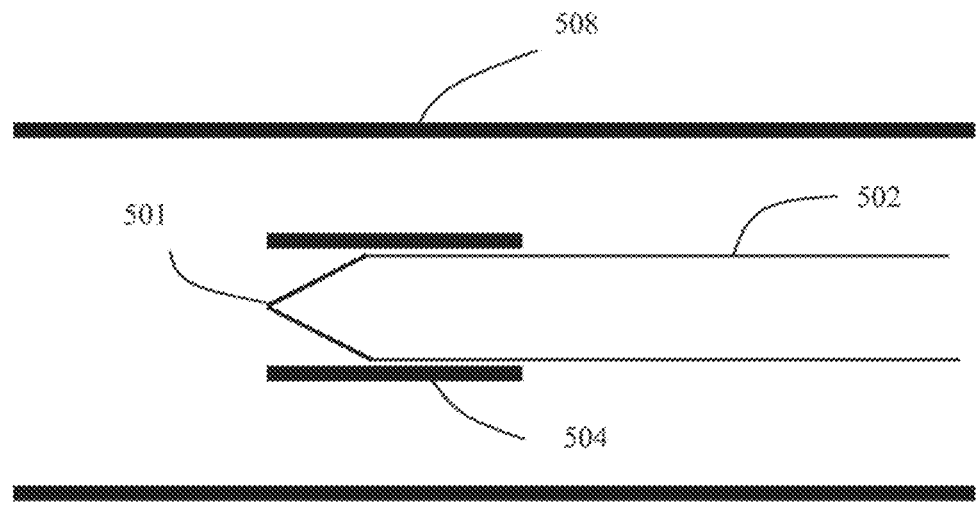
Figure 23B:
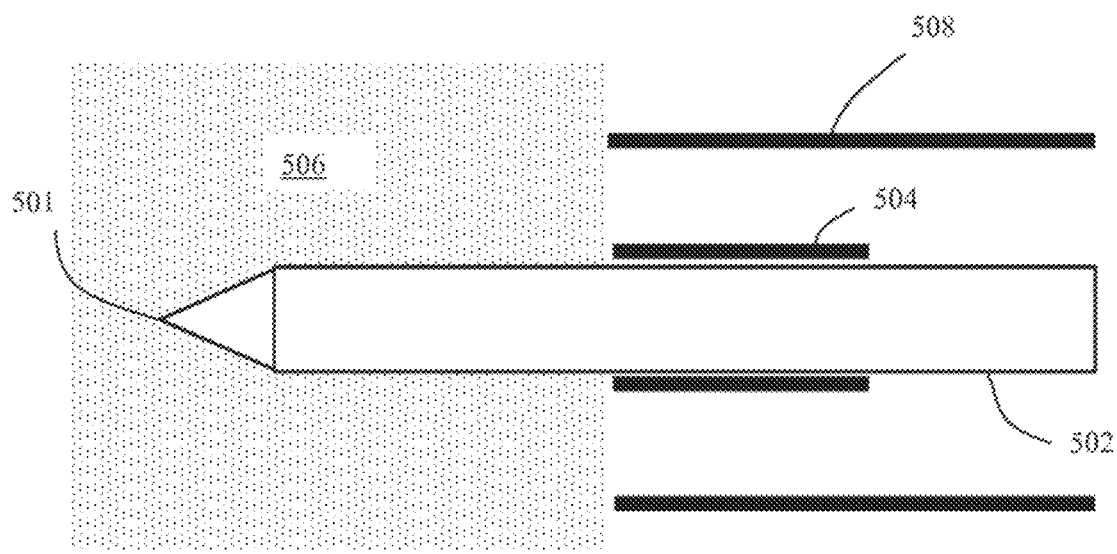
Figure 24A:
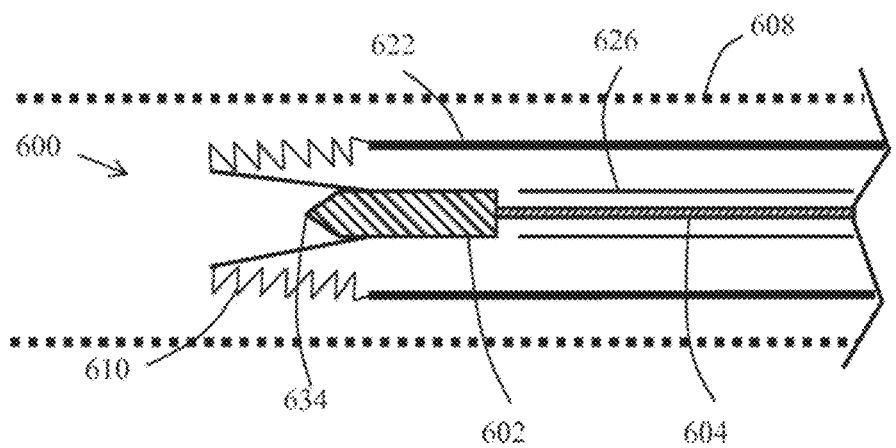
Figure 24B:
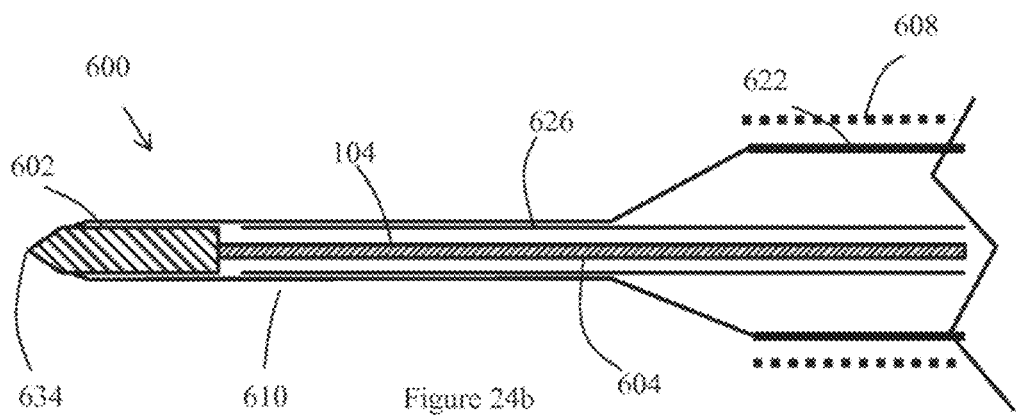
Figure 24C:
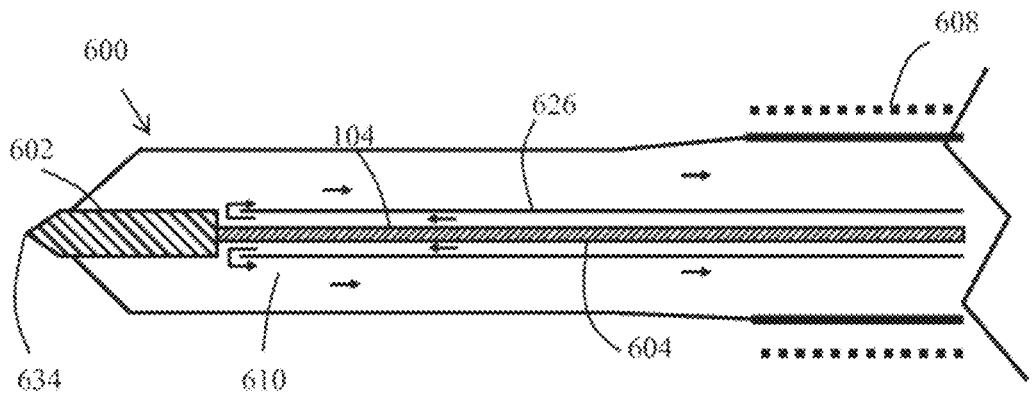
Figure 25A:
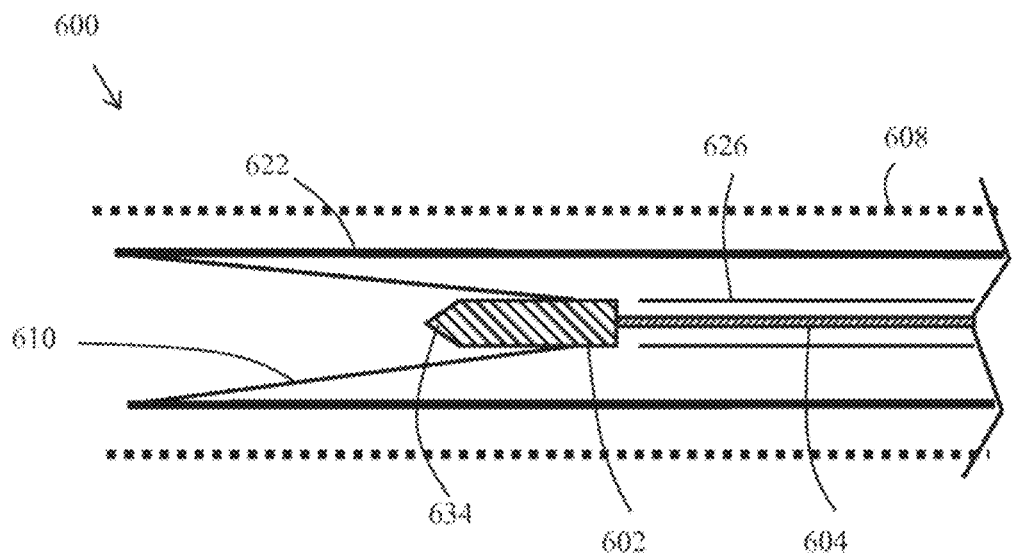
Figure 25B:
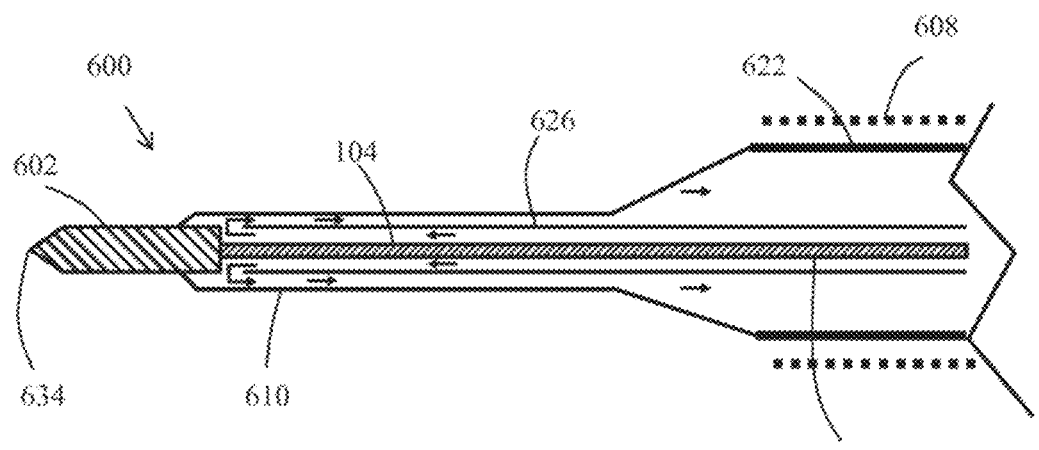

FIGS. 5a, 5b, and 5c show cross section views through a catheter portion of an ablation probe according to different embodiments;

FIG. 6a shows a close up view of the boundary between the needle portion and the catheter portion of the ablation probe shown in FIG. 2;

FIG. 6b shows a perspective view of an ablation probe having an tube formed from an elastic material extending from the distal end of a working channel along which it is inserted;

FIG. 6c shows a perspective view of an ablation probe without a tube formed from an elastic material extending from the distal end of a working channel along which it is inserted;

FIG. 7 shows a close up view of a tube forming part of the ablation probe shown in FIG. 2;

FIG. 8a shows another close up view of an embodiment of an applicator which may form part of the ablation probe shown in FIG. 2;

FIG. 8b shows a close up view of a bridging tube according to an embodiment;

FIG. 9 shows a close up view of an applicator forming part of the ablation probe shown in FIG. 2;

FIG. 10a shows a cross section view of an applicator of an ablation probe according to another embodiment;

FIG. 10b shows a cross section view of an applicator of an ablation probe according to another embodiment;

FIG. 11a shows another cross section view of an applicator of an ablation probe according to another embodiment FIG. 11b shows a close up view of a part of a needle portion of an ablation probe according to an embodiment;

FIGS. 12a and 12b show schematic side and cross section views of an inflation member of the ablation probe of an embodiment moving between an inflated and deflated configuration;

FIGS. 13a and 13b show schematic side and cross section views of an inflation member of the ablation probe of another embodiment moving between an inflated and deflated configuration;

FIG. 14 shows another close up view of a part of a needle portion of an ablation probe according to an embodiment;

FIG. 15 shows another close up view of a part of a needle portion of an ablation probe according to an embodiment;

FIG. 16 shows a cross section through a needle portion of an ablation probe according to an embodiment;

FIG. 17 shows another close up view of a part of a needle portion of an ablation probe according to an embodiment;

FIGS. 18a and 18b show an off-axis deformable member according to an embodiment;

FIG. 19 shows a close up cross section view of a choke element according to an embodiment;

FIG. 20 shows a cross section view of a choke formed by a tube housing a feeding cable of the ablation probe, an outer conductor of the feeding cable and a conducting coating at a proximal end of an applicator of the ablation probe;

FIG. 21 shows a cross section view of a connector arranged to connect the distal and proximal portions of a feeding cable according to an embodiment;

FIGS. 22a and 22b show a schematic view of part of an ablation probe according to another embodiment;

FIGS. 23a and 23b show an embodiment of an ablation probe comprising a sheath member and FIGS. 24a, 24b show an ablation probe in a sheathed and an unsheathed configuration respectively;

FIG. 24c shows an ablation probe in an unsheathed configuration with the deformable member moved to a deployed configuration; and FIGS. 25a and 25b show an ablation probe in a sheathed and an unsheathed configuration respectively.

Figure 1A:
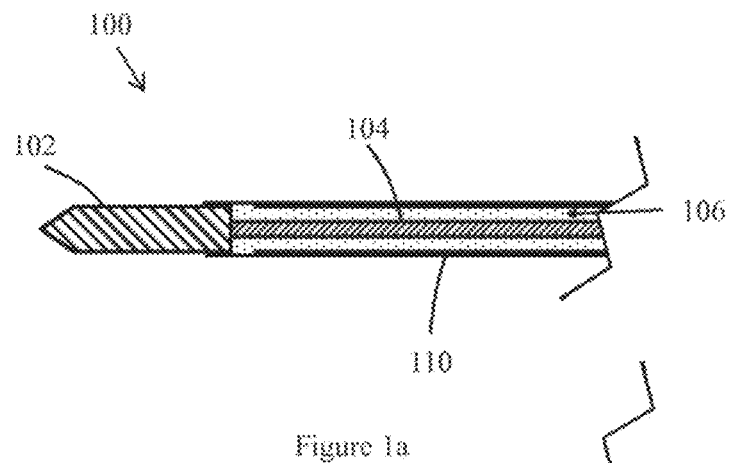
FIGS. 1a and 1b show a schematic view of part of an ablation probe according to an embodiment.
Figure 1B:
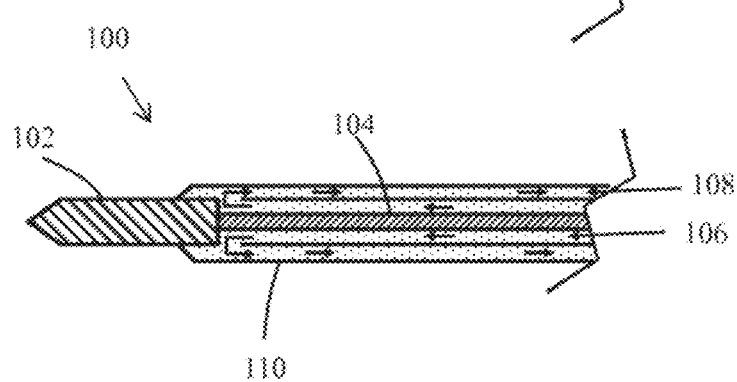

An ablation probe 100 according to one embodiment is shown schematically in FIGS. 1a and 1b. The ablation probe 100 of the present disclosure may be suitable for insertion into the body to reach a desired treatment site, such as a malignant tissue growth. In order to reach a desired treatment site, the ablation probe may be suitable for insertion through the working channel of an internal anatomy access device. By internal anatomy access device we mean any device which may be placed within the anatomy of a patient, the device having a working channel for insertion of instruments to a desired location within the body. The internal anatomy device may be an intraluminal delivery device arranged to be delivered along an anatomical lumen of the patient (e.g. the trachea and the pathways of the bronchi in the lungs or the oesophagus). The ablation probe 100 may, for example, be used endoscopically in order to reach a variety of disease locations within the body. The ablation probe may therefore have an overall flexibility such that it can be inserted through the working channel of the endoscope. In other embodiments, the ablation probe may be used with other types of intraluminal delivery device such as specific types of endoscope (e.g. a bronchoscope) or a navigation system such as a lung navigation system. In other non-claimed examples, the ablation probe 100 may also be used percutaneously, or using any other suitable technique, e.g. inserted through an existing aperture of the body. For percutaneous use, the ablation probe may be generally rigid so that it can be inserted.

The ablation probe 100 comprises an applicator 102 arranged to apply radiation to heat surrounding tissue. The applied radiation may be adapted to cause localised heating and destruction of malignant cells around or near to the applicator 102. The applicator 102 may be arranged to apply any suitable form of radiation to surrounding tissue such that the desired heating is caused. The applicator 102 may, for example, be arranged to emit microwave or RF radiation, or may emit any other suitable radiation to cause heating. The applicator 102 may be arranged at or near a distal end of the ablation probe 100 so that it can be positioned in a desired position relative to the tissue to be treated. In the following, the terms "distal" and "proximal" are taken relative to the user operating the ablation probe and the treatment site when the ablation probe is positioned for use—the distal end of the ablation probe 100 is that closest to the treatment site and the proximal end is that closest to the user. A control means (not shown in the Figures) such as a handle may be provided at the proximal end of the ablation probe 100 so that it can be manipulated and positioned by the user.

The ablation probe 100 further comprises a feeding cable 104 which is arranged to supply electromagnetic energy to the applicator 102. The feeding cable may be any elongate member suitable for supplying electromagnetic energy to the applicator (e.g. a conductor). The feeding cable 104 may run along at least part of the length of the ablation probe 100 to deliver a supply of energy to the applicator 102. In the described embodiment, a distal end of the feeding cable 104 is coupled to a proximal end of the applicator 102 and a proximal end of the feeding cable 104 is coupled to a generation means (not shown in FIGS. 1a or 1b) suitable for generating the desired signal to supply energy to the applicator 102.

The ablation probe 100 further comprises a first coolant path. In the described embodiment, the first coolant path is a coolant delivery path 106 via which coolant is able to flow towards the applicator 102. For example, the coolant delivery path 106 may deliver a flow of coolant towards the distal end of the ablation probe 100 from a coolant supply means (not shown in the Figures) coupled to the coolant delivery path 106 at the proximal end of the ablation probe 100. The flow of coolant may help control the temperature of the ablation probe 100 during use. This may allow energy to be delivered to the surrounding tissue for an extended period of time without the ablation probe 100 overheating and being damaged, or causing injury to healthy tissue. The coolant delivery path may be formed by one or more coolant channels as will be described later. The coolant may be a fluid, and may be water, saline solution, a cryogenic gas or any other suitable coolant known in the art.

The ablation probe 100 further comprises a second coolant path. In the described embodiment, the second coolant path is a coolant return path 108 via which coolant can return from the applicator. The coolant return path 108 may therefore return the supply of coolant from the distal end of the ablation probe 100 to the proximal end. The ablation probe 100 further comprises a deformable member 110 which is arranged to move between an insertion configuration (shown in FIG. 1a) in which insertion of the ablation probe 100 is facilitated and a deployed configuration (shown in FIG. 1b). When in the deployed configuration, the coolant return path 108 is provided by the deformable member 110. In some embodiments, no coolant return path may be provided when the deformable member is in the insertion configuration. This may allow the profile of the ablation probe to be minimised. In other embodiments, the return path may not be completely absent when the deformable member is in the insertion configuration. The insertion configuration therefore provides a configuration in which the ablation probe 100 may be suitable for delivery to the desired location within the body. The insertion configuration may, for example, correspond to a suitable size and/or shape adapted to allow insertion with reduced risk of undesired tissue damage. When in the insertion configuration, the ablation probe 100 may, for example, have a low profile (e.g. small cross sectional size) for ease of insertion through tissue without causing injury or insertion through the working channel of an endoscope.

In other embodiments, the first coolant path may act as a coolant return path. In this embodiment, the first coolant path is arranged to carry a flow of coolant away from the applicator. In this embodiment, the second coolant path may act as a coolant delivery path arranged to carry a flow of coolant towards the applicator. A combination of the first and second coolant paths may therefore form a coolant circuit arranged to deliver a flow of coolant to and away from the applicator, where the coolant can flow in either direction along each of the first and second coolant paths. In the embodiment shown in the figures, the first coolant path acting as the coolant delivery path may allow a flow of colder coolant close to the feeding cable. This may aid cooling of the ablation probe as a significant amount of heat may be generated in the feeding cable. In other embodiments, where the second coolant path acts as the coolant delivery path, colder coolant may be delivered to the applicator first to aid cooling of the applicator.

The ablation probe 100 may therefore be delivered to the desired location whilst the deformable member 110 is in the insertion configuration. Once at the desired location, the deformable member 110 may be moved to the deployed configuration to allow flow of the coolant away from the applicator 102. The coolant can then flow via the coolant delivery and return paths to cool the ablation probe 100 during use. The deformable member 110 therefore is able to provide an insertion configuration suitable for delivery to the ablation site when the coolant flow is not required. Once the ablation probe is in position, the deformable member 110 may be moved to a configuration suitable to provide a flow of coolant as required during delivery of energy from the applicator 102. When in the deformable member is in the insertion configuration the overall diameter of the ablation probe may be between about 13 to about 25 gauge (approximately 2.5 to 0.5 mm). This may allow easy insertion.

As can be seen in FIGS. 1a and 1b, the coolant return path 110 may be provided only by the deformable member along at least a portion of a length of the ablation probe 100. For example, along at least part of the length of the ablation probe 100, no other channels or conduits to carry returning coolant may be provided in addition to the coolant return path 108 formed by the deformable member 110. This may allow the ablation probe 100 to have a small cross sectional size when the deformable member is in the insertion configuration. Any additional coolant return paths would require additional space within the body of the ablation probe 100 and so would not provide a low profile.

In the embodiment of FIGS. 1a and 1b, the deformable member 110 is fluidly connected to a distal end of the coolant delivery path 106 (e.g. the distal end of the coolant delivery path may be joined to the distal end of the fluid return path to form a single path along which coolant may flow towards and then away from the applicator (in either direction)). The coolant delivery path 106 therefore runs along the inside of the coolant return path 108 when the deformable member 110 is in the deployed configuration. This arrangement allows the overall size of the ablation probe 100 to be reduced when the deformable member 110 is in the insertion configuration.

An example embodiment of an ablation probe 200 according to this disclosure is shown in more detail in FIGS. 2 to 8a. The embodiment shown in the Figures is only one such example.

As can be seen in FIG. 2, in this embodiment, the ablation probe 200 generally comprises two portions: a needle portion 212 and a catheter portion 214. The needle portion 212 may be arranged at the distal end of the ablation probe 200 and is adapted to be inserted into tissue during use to reach the desired ablation location. The catheter portion 214 may be provided at the proximal end of the ablation probe 200 and is arranged to supply electromagnetic energy and a flow of coolant to and from the needle portion 212. In the embodiment shown in the Figures, the ablation probe 200 further comprises a handle portion 216 via which the ablation probe may be manipulated and positioned during use. The catheter portion may have an extended length and flexibility for endoscopic use as shown in FIG. 2. In other non-claimed embodiments, a shorter, more rigid catheter portion may be provided for percutaneous use.

In some embodiments, the needle portion may form a small part of the overall length of the ablation probe. For example, the needle portion may be 5 mm to 2000 mm in length, and preferably may be around 70 mm in length. The length of the needle portion may be chosen according to the anatomy to be accessed. For example, the needle portion may be approximately between 10 and 100 mm long for delivery of therapy to organs including the pancreas, or lung, or longer (for example 100-400 mm in length) for delivery of therapy percutaneously. A longer length of needle portion may be more suitable for accessing parts of the lung, for example. The catheter portion may be around 1000 mm to 2000 mm in length, and preferably around 1400 mm in length. The length of the catheter portion may be chosen according to the position of the ablation site which must be reached. In other embodiments, the needle portion of the ablation probe (e.g. that having the deformable member) may form a greater proportion of the length of the ablation probe. In some embodiments, the entire length of the ablation probe may be formed by the needle portion. In such an embodiment, the deformable member may extend along the majority or all of the length of the ablation probe. In such an embodiment, the catheter portion may not be required. For example, if the ablation probe is to be used percutaneously the catheter portion may be shorter than for endoscopic use, or may not be required.

Figure 3:
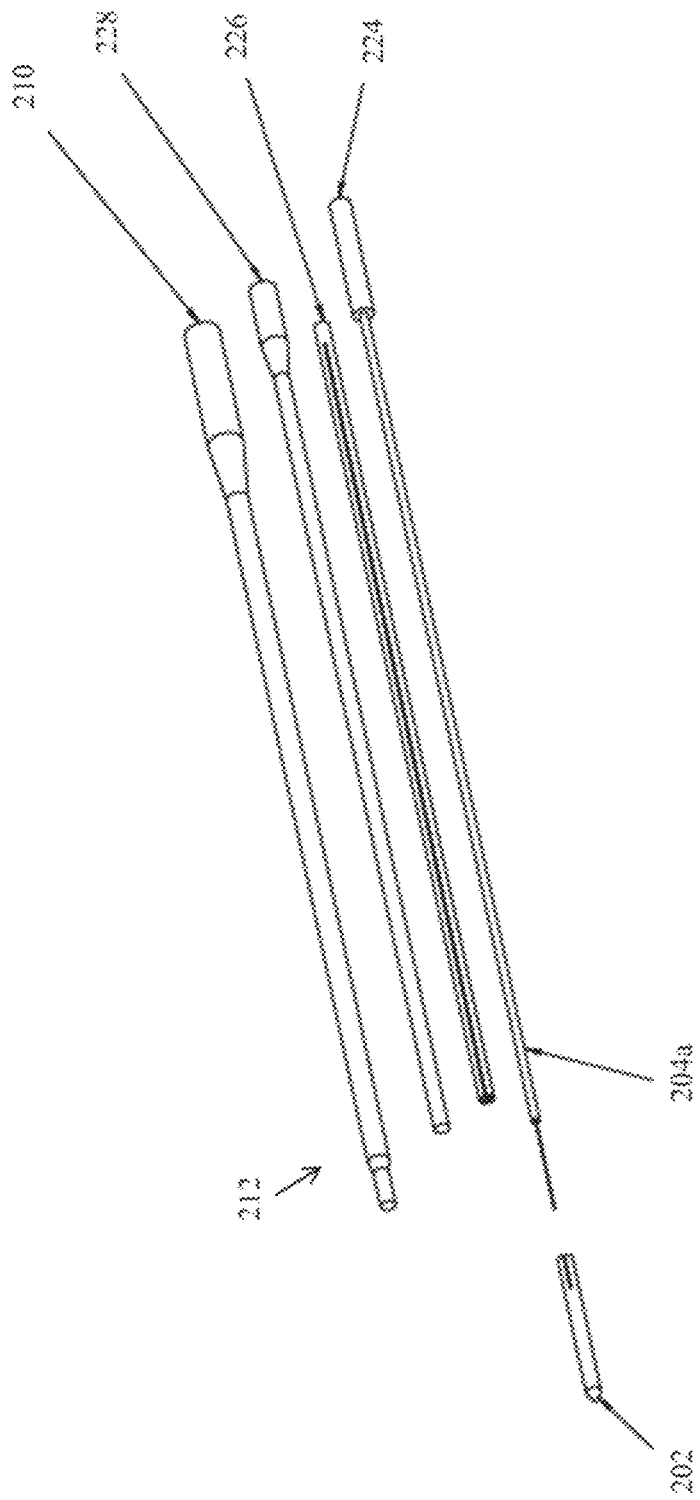
FIG. 3 shows an exploded view of a needle portion of the ablation probe shown in FIG. 2.
Figure 4:
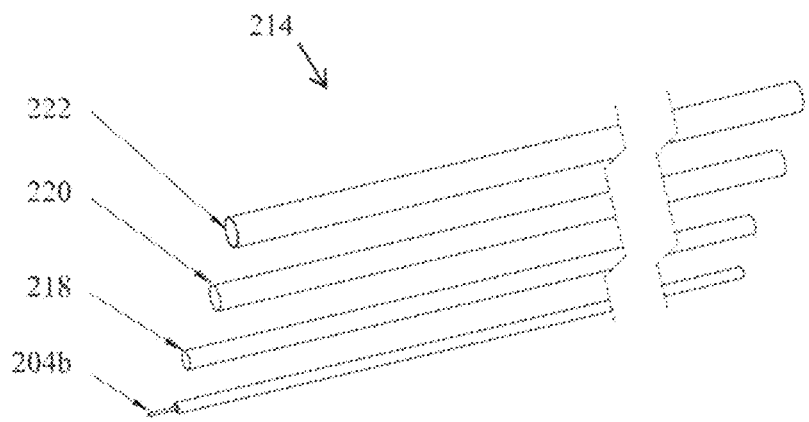
FIG. 4 shows an exploded view of a catheter portion of the ablation probe shown in FIG. 2.

An exploded view of the needle portion is shown in FIG. 3. The needle portion 212 may comprise a deformable member 210, an applicator 202, a distal portion of the feeding cable 204a and a distal portion of the coolant delivery path. An exploded view of the catheter portion is shown in FIG. 4. In this embodiment, the catheter portion 214 may comprise a proximal portion of the feeding cable

204b, a proximal portion of the coolant delivery path, and a coolant return conduit (which may be non-deformable). The proximal portion of the coolant delivery path may be formed by a space between a tube 218 housing the proximal portion of the feeding cable 204b and a surrounding coolant delivery tube 220. The coolant return path may be formed by a space between the coolant delivery tube 220 and a surrounding coolant return tube 222. In other embodiments, any other suitable arrangement of channels or conduits may be provided to form the coolant return and coolant delivery paths within the catheter portion 214.

The greatest cross sectional size of the needle portion may be less than the greatest cross sectional size of the catheter portion. In other words, the cross section size (e.g. diameter) of the needle portion at its largest point may be less than the cross sectional size (e.g. diameter) of the catheter portion at its greatest point. This may allow the needle portion to access an ablation site whilst reducing any potential for tissue damage. The catheter portion on the other hand may be sized to fit through the working channel of the device with which it is used.

Examples of suitable arrangements of channels forming the coolant return and coolant delivery paths are shown in the cross sectional views of FIGS. 5a to 5c. In FIG. 5a, the catheter portion comprises two lumens each forming one of the coolant return and coolant delivery paths. In FIG. 5b, the catheter portion comprises four lumens forming the coolant return path and coolant delivery path. Two of the lumens may form the coolant return path, and two of the lumens may form the coolant delivery path. This embodiment may provide better kink resistance and strength. The lumens may not be equally sized as shown in FIGS. 5a and 5b. An example of this is shown in FIG. 5c in which three lumens are provided. A first and second lumen may provide the coolant return and delivery paths, with the third lumen provided to include other components such as a sensor or the like. The third lumen may be small in size compared to the first and second lumens to provide adequate space for the flow of coolant.

In other embodiments, the channels forming the coolant return and coolant delivery paths within the catheter portion may be formed by one or more channels in the outer conductor of the proximal portion of the feeding cable. This may improve flexibility and provide a compact arrangement.

In the described embodiment, the feeding cable is formed by two lengths of cable (the distal portion 204a and the proximal portion 204b) joined at the boundary between the needle portion 212 and the catheter portion 214 (shown in more detail in the close up view of FIG. 6). The feeding cable may be formed by two lengths of coaxial cable to form an electrical circuit to deliver electromagnetic energy to the applicator 202. In other embodiments a single feeding cable may be used having regions of different thickness to form the distal and proximal portions. In other embodiments, any other suitable conductor may be provided to deliver a supply of suitable electromagnetic energy to the applicator 202. The ablation probe 200 may further comprise a connector 224 arranged to mechanically and electrically splice the distal portion of the feeding cable 204a to the proximal portion of the feeding cable 204b. The connector 224 may connect the different portions of the feeding cable 204a, 204b while maintaining an effective impedance match, minimising electrical losses and ensuring a compact configuration of the ablation probe 200. An example of a connector used to connect the different portions of the feeding cable is shown in more detail in FIG. 21 and is described later.

In the described embodiment, the distal portion of the feeding cable 204a has a corresponding distal cross sectional size, and a proximal portion of the feeding cable 204b has a corresponding proximal cross sectional size, wherein the distal cross sectional size is less than the proximal cross sectional size. The size (e.g. diameter) of the conductor is therefore optimised based on its position within the ablation probe 200. The cross sectional sizes may be chosen to optimise (e.g. maximise) the feeding cable power handling, while also reducing electrical losses and optimising the mechanical strength of the ablation probe 200. In other words, the length of the smaller cross section portion of the feeding cable is minimised by connecting it to a larger cross section feeding cable (e.g. a more efficient cable) for the portion of the ablation probe 200 outside of the needle portion 212. This part of the ablation probe 200 does not need to be inserted into tissue so a small profile is not as important. The cross section of the feeding cable in the catheter portion 212 is therefore increased to reduce power loss where a small cross section is less important.

The needle portion of the ablation probe may therefore have a smaller overall cross sectional size compared to the catheter portion. The needle portion is therefore optimised for insertion into tissue, whilst the catheter portion is optimised for power delivery over the long length of a device working channel through which it is inserted. In use, only the needle portion may protrude from the working channel through which the ablation probe is inserted. It is therefore important for the needle portion to have a relatively small cross sectional size to reduce tissue damage. For the catheter portion a relatively larger cross sectional size can be used. Compared to the needle portion, the catheter portion is instead optimised for power delivery along the length of the working channel. In one example, the needle portion, when the deformable member is in the insertion configuration, may have an overall diameter of 1 mm at its largest point. The catheter portion may have an overall diameter of 3 mm at its largest point.

In other embodiments, the cross sectional size of the distal and proximal portions of the feeding cable may be the same. In this case, a reduction in overall size of the needle portion compared to the catheter portion may still be provided by the use of the deformable member.

The needle portion 212 may further comprise a tube 226 (e.g. a hypotube) arranged to house the distal portion of the feeding cable 204a. The tube 226 may be formed from a metal material which has sufficient rigidity to allow the needle portion 212 to be inserted into tissue. In other embodiments, the tube 226 may be formed from any other suitable material and may be formed from a superelastic material, for example Nitinol.

In other embodiments, the tube 226 may be formed form an elastic material (and not specifically a superelastic material). By forming the tube from an elastic (or superelastic) material it may withstand permanent deformation after being delivered through the tortuous path of a working channel. As the ablation probe extends from the working channel it may consequently follow a straight path, rather than following a curved path caused by the material being deformed by the shape of the working channel. This may help to more easily guide the distal tip of the ablation probe to the desired position.

An example of this is shown in FIGS. 6b and 6c. FIG. 6b shows an example of an ablation probe 200 having a tube formed from an elastic material extending from the end of the working channel 201 through which it has been inserted. The portion of the ablation probe extending from the working channel can be seen to follow a straight path. FIG. 6c shows an example of an ablation probe with a non-elastic tube. This figure illustrates how the portion of such an ablation probe extending from the working channel 201 tends to follow a curved path.

In some embodiments, the tube may be formed from an elastic (or superelastic) electrically conducting material. This may allow the tube to form part of a choke as will be described later. The tube may be formed from a solid material or a mesh material as appropriate to allow the required elasticity, for example a braid or coil reinforced polymer tube.

In one embodiment, the coolant delivery path is provided by a channel formed between the feeding cable and inside wall of the tube 226. For example, clearance between the feeding cable and the inside wall of the tube 226 may provide space for coolant to flow. In other embodiments, slots may be cut into the inside wall of the tube 226 to provide a space through which coolant can flow. The amount of clearance may be specified to ensure an adequate flow of cooling is achieved while maximising the power carrying capacity of the feeding cable.

In the embodiment shown in the Figures, the coolant delivery path comprises one or more coolant channels formed in the body of the tube 226. The coolant therefore may partly surround the feeding cable to aid cooling. The width and number of the channels may be chosen to optimise (e.g. maximise) the mechanical strength of the ablation probe 100 and the performance of the cooling.

The one or more channels may be cut into the wall of tube 226 to allow cooling fluid to flow adjacent to the distal portion of the feeding cable 204a. In the described embodiment, the one or more channels may be formed by one or more slots formed in the outer surface of the tube 226. In this embodiment, the ablation probe 200 may further comprise a membrane 228 disposed around the tube 226. The membrane 228 may be arranged to separate the coolant delivery path from the coolant return path (e.g. it forms a boundary between them). In some embodiments, the one or more channels may extend distally past a distal end of the membrane 228 so that coolant can flow from the one or more channels into the deformable member 210. In other embodiments, one or more apertures may be provided in the membrane 228 to fluidly connect the one or more channels with the deformable member 210. The membrane 228 may be formed from a thin layer of material (for example a polymer heat shrink) located over the tube 226 to form an enclosed conduit for the cooling fluid. In other embodiments, the channels may be formed within the wall of the tube 226, in which case the membrane 228 may not be required.

In other embodiments (not shown in the Figures), the distal portion of the feeding cable 204a may comprise an inner conductor arranged to transmit a signal to the applicator 202 and an outer conductor arranged to shield the inner conductor (e.g. it may be a coaxial cable). The coolant delivery path may comprise one or more coolant channels formed in the outer conductor. The coolant channels may, for example, be formed by one or more slots in an outer surface of the outer conductor. The coolant and the split outer conductor may thus form a mixed media outer conductor arranged to shield the electrically insulating material. A membrane may be formed around the outer conductor to form a conduit for the cooling fluid. In some embodiments, the feeding cable may be formed by a coaxial cable in which the outer conductor is manufactured from a robust material (for example stainless steel) to form a ridged body of the needle portion. In this embodiment, the coolant delivery path may be formed by channels in the outer conductor, rather than in the tube 228. In such an embodiment, the tube may therefore not be required, thus saving space. In other embodiments, the tube may also be provided. The cooling channels may also more effectively cool the feeding cable as well as deliver coolant to the applicator 202. In some embodiments, the one or more channels formed in the outer conductor may be aligned with the central axis of the feeding cable. The width and number of the channels may be chosen to optimise the mechanical strength of the feeding cable and the performance of the cooling, while minimising electrical losses and ensuring impedance matching between portions of the feeding cable having channels in the outer conductor and portions of the feeding cable in which the channels are not present (e.g. in the catheter portion).

The one or more coolant channels described above forming the coolant delivery path may be disposed along a length of the ablation probe as can be seen in the close up view of the tube 226 shown in FIG. 7. In some embodiments, a plurality of channels may be provided such that they are spaced equally around a circumference of the outer conductor or tube 226 housing the feeding cable. In FIG. 7 only one of the channels is visible (labelled 230). In some embodiments, the plurality of channels may comprise four channels spaced equally around the circumference of the outer conductor or tube 226 housing the feeding cable. In other embodiments, other numbers and arrangements of channels may be provided according to the cooling requirements and mechanical strength requirements of the ablation probe.

The inner conductor of the distal portion of the feeding cable 204a is coupled to the applicator 202 as shown in the detailed view of FIG. 8a. In this embodiment, a distal end of the distal portion of the feeding cable is connected to a proximal end of the applicator 202. Where the feeding cable is formed from an inner and outer conductor, the inner conductor may be attached to the applicator 202 to ensure efficient transfer of electromagnetic energy to the applicator material. The applicator 202 may be formed from a ceramic material with suitable dielectric properties (for example zirconia) according to the energy it is arranged to apply. An internal bore may be provided in the applicator 202 to receive a portion of the inner conductor to ensure a strong mechanical joint that may also be glued in position. The applicator 202 may further be coupled to the tube 226 housing the feeding cable where it is provided. In such an embodiment, the proximal end of the applicator 202 may be connected to the tube 226 via a bore to receive the tube or a set of interlocking fingers to maximise the mechanical strength of the bond between them. In other embodiments, any other suitable connection means between the tube 226 and the applicator 202, or the distal portion of the feeding cable 204a and the applicator 202 may be provided.

In one embodiment, a bridging member may be provided to couple the tube 226 and the applicator 202. In the example shown in the FIG. 8b, the bridging member comprises a bridging tube 226b surrounding a part of the tube 226 and the applicator 202 so that it bridges the connection between them. A tight fit may be provided between the bridging tube 226b and each of the tube 226 and applicator 202 to secure them together. This may help to provide improved mechanical strength in the joint between the tube 226 and the applicator 202. This may be advantageous when the ablation probe is delivered through a working channel having a tortuous route through the anatomy of the patient. The bridging tube 226a may be formed from a heat resistant material such as a polyimide (PI) material. This may help allow the bridging tube 226a to withstand the heat generated by the applicator 202. In other embodiments, any other suitable material may be used. The bridging tube 226a may be a thin walled tube so as to minimise the overall cross sectional size of the needle portion. The thickness of the walls of the bridging tube 226a may, for example, be in a range of 0.01 to 0.15 mm. In some examples the bridging tube may be constructed from a heat resistant material, for example a thermoset or polyamide.

In some embodiments, the applicator 202 may further comprise one or more coolant channels 232 fluidly connected to the coolant delivery path. In this embodiment, the channels may be formed in the applicator 202 as shown in the close up view of the applicator 202 shown in FIG. 9. The channels 232 may allow the cooling fluid to flow past the applicator surface toward the distal tip of the applicator 202 (e.g. along part of or all of the length of the applicator 202). A thin layer of material (for example a polymer heat shrink) may be arranged over the applicator to enclose the channels 230 and form a conduit for the cooling fluid. This arrangement may reduce the risk of tissue charring at the antenna surface and associated losses in heating performance. In some embodiments, the one or more channels 232 in the applicator may extend partially along the length of the applicator from the proximal end as shown in FIG. 9 to target the cooling fluid to allow a controlled ablation heating zone to be generated.

FIG. 10a shows another example of applicator coolant channels. One or more applicator coolant channels may be formed by one or more recesses in an outer surface of the body of the applicator 202. An example of this is shown in FIG. 10a where a coolant channel 232a can be seen in the applicator 202. In this example, the coolant channel 232a is formed by a recess running around the circumference of the outer surface of the applicator 202. This may help to provide a suitable flow of coolant around the applicator 202 to aid cooling. In other embodiments, other shapes and numbers of coolant channels may be provided. In the embodiment shown in FIG. 10a the applicator 202 is partly surrounded by the deformable member 210. The applicator coolant channel(s) 232a may be fluidly coupled to the deformable member 210 such that they allow a flow of coolant into the coolant return path (or from the coolant delivery path if the flow of coolant were to be reversed). The coolant may therefore flow into a proximal end of the applicator coolant channel(s) 232a, along the length of the applicator 202 and into the deformable member 210 (or vice versa). In other embodiments, other arrangements of applicator coolant channels may be provided. They may, for example, be disposed within the body of the applicator, rather than being recesses in its surface.

The ablation probe may further comprise an insulating member 233 which is disposed between the deformable member 210 and the applicator 202 as shown in FIG. 10a. The insulating member 233 may help to shield the deformable member 210 from heat produced by the applicator 210. The insulating member 233 may be formed by a heat resistant tube extending at least partly around the body of the applicator 202. The insulating member 233 may be formed from a material such as a polyimide to provide suitable heat resistance. In other embodiments, other materials may be used where appropriate. The insulating member 233 may be formed from a thin-walled tube to reduce the overall cross-sectional size of the needle portion. The walls may be, for example, 0.01 to 0.15 mm thick. It may be constructed from a heat resistant material, for example a thermoset or polyamide.

The applicator 202 may comprise an insertion region 202a arranged to extend into the tube 226 which houses the distal portion 204a of the feeding cable. An example of this is shown in FIG. 10b, which shows a cross section through the tube 226 and the insertion region 202a of the applicator 202. The insertion region may comprise one or more channels arranged to fluidly couple the first coolant path to the applicator coolant channels described above. In the embodiment shown in FIG. 10b two channels 233c, 233d arranged to fluidly couple the first coolant path and the applicator coolant channels 232a, 232b are shown. By providing an insertion region 202a having one or more coolant channels a secure mechanical connection can be provided between the tube 226 and the applicator 202 whilst still facilitating coolant flow. The mechanical connection may be supplemented by an adhesive as required to improve the connection. In the embodiment shown in FIG. 10b the channels 232a, 232b are formed by flats cut into the surface of the insertion region 202a of the applicator 202. This may provide a compact and easily manufactured arrangement. In other embodiments, any other suitably arranged or shaped channels may be provided.

In the described embodiment, the ablation probe 202 may comprise a pointed tip adapted to pierce tissue during use. In embodiments where the applicator 202 is located at the distal end of the ablation probe 200, the distal end of the applicator 202 may form the pointed tip (labelled 234 in FIG. 9). The distal tip of the applicator 202 may therefore be pointed to ensure the applicator 202 can effectively pierce through tissue for delivery to the ablation site.

The ablation probe may further comprise a coupling member 236a arranged to couple the deformable member to the applicator. An example of such a coupling member 236a is shown in FIG. 10a. The coupling member 236a may be formed from a material different from the applicator 202. The coupling member 236a may be arranged to form a bonding site to which the deformable member 210 is bonded. The deformable member 210 may be bonded to the coupling member 210 using an adhesive or similar bonding compound. By forming the coupling member 210 from a material that is different from the applicator 202 a material more suitable for bonding to the deformable member 210 may be chosen. This may provide an improved bond compared to connecting the deformable member and the applicator directly to each other. The coupling member 236a may, for example, be formed from a plastics material such as a polyimide material. This may allow a strong bond to be formed with the deformable member 210, and also provide suitable resistance to heat generated by the applicator 202 during use.

The coupling member 236a may be shaped to form a mechanical coupling with the applicator 202. In the embodiment shown in FIG. 11a, the coupling member 236a is formed from a coupling tube surrounding the applicator 202, the tube having a close fit with the outer surface of the applicator 202 to form a friction fit between them. The tube forming the connecting member may be a thin walled tube to minimise the overall cross section. The walls of the tube may, for example, have a thickness between ?? and ?? mm. In other embodiments, an alternative mechanical coupling may be provided.

An alternative coupling member 236b is shown in FIG. 11b. In this embodiment, the ablation probe 200 may further comprise a coupling member 236a formed from an electrically insulating material coupled to the distal end of the applicator 202. In the embodiment shown in the Figures, a separate tip member 238 comprising a pointed tip is coupled to the coupling member 336a to form the pointed tip at the distal end of the ablation probe 200. In other embodiments, the tip member 238 and the coupling member 236a may be formed by a single component. The coupling member 236a may be formed from a material with a low electrical permittivity (e.g. a polymer). In this embodiment, heating effects may be confined (or partly confined) to the applicator 202, thus providing a cool portion onto which the deformable member 210 can be bonded such that it is coupled to the applicator 202 via the coupling member 236a. Furthermore, the flexural stiffness of the coupling member 236a may be chosen to optimise the flexibility of the ablation probe 200 to facilitate delivery within a tortuous anatomy (for example in the lung). In other embodiments, a coupling member may additionally or alternatively be provided at the proximal end of the applicator 202 to provide a coupling between the deformable member and the proximal end of the applicator 202.

The coupling members 236a, 236b shown in FIGS. 11a and 11b are only one such example of a coupling member that may be provided to connect the deformable member 210 to the applicator 202. In other embodiments, a coupling member may have any other suitable shape according to the geometry of the applicator 202 and deformable member 210. In yet other embodiments, the coupling member may be absent, with a direct connection formed between the deformable member and the applicator.

In other embodiments, the probe may comprise a blunt tip adapted to prevent or reduce the piercing of tissue during use. In such an embodiment, the applicator 202 or coupling member 236b may have a blunt distal end which is less likely to pierce tissue during use. This may be advantageous for some treatment sites such as in the lungs.

The needle portion further comprises the deformable member 210 as shown in the exploded view of FIG. 3. In the described embodiment, the deformable member 210 is formed by an inflatable member arranged to move between a deflated configuration when the deformable member 210 is in the insertion configuration and an inflated configuration when the deformable member 210 is in the deployed configuration. The inflatable member may thus form a balloon which may be inflated by the flow of coolant (e.g. the inflatable member may inflate due to the pressure of the coolant). In the described embodiment, the inflatable member has an inside diameter that matches the outside diameter of the tube 226 (or the membrane 228 surrounding the tube 228 or the outer conductor or insulating material respectively). The inflating member may inflate to a larger diameter when the cooling system is pressurised. This may therefore form a conduit for the cooling fluid to return from the applicator 202. When moving to the inflated configuration, some, or all, of the inflating member may change shape (e.g. expand) to allow space for the coolant to flow. When the inflation member is deflated, the insertion profile of the ablation probe 200 may be reduced (e.g. minimised) to aid delivery to the target ablation site. When the ablation therapy has been delivered, the inflation member may be deflated so that it returns to its original diameter to facilitate removal.

The inflatable member may be arranged to inflate or expand to a maximum threshold size in the inflated deployed configuration. This may facilitate easy insertion of the ablation probe 200. In some embodiments, the inflatable member may comprise a compliant or semi-compliant material arranged to expand or contract in size in order to move between the deflated insertion and inflated deployed configurations. The inflatable member material and geometry may have the necessary properties to allow it to expand by a suitable amount and elastically to return to its original shape or diameter. In some embodiments, a vacuum may be applied to the coolant return path after therapy delivery to help the inflatable member to collapse and aid removal of the ablation probe 200. The vacuum may be provided in addition to, or to replace, the elastic function of the inflatable member. The inflatable member may be formed from a thin wall material to minimise the overall profile of the ablation probe 200. In some embodiments, the inflatable member may have low friction properties or may be coated with a lubricious material (for example parylene) to aid insertion. In some embodiments, the inflatable member material (or coating) may also allow the inflatable member to be easily separated from the other components forming the ablation probe when it inflates (e.g. the membrane). An example of the compliant or semi-compliant deformable member 110 moving from the deflated to the inflated configurations is shown schematically in FIGS. 12a and 12b.

In other embodiments, the inflatable member may be formed from a non-compliant material arranged to fold or unfold in order to move between the deflated insertion and inflated deployed configurations. In this embodiment, the inflatable member may be wrapped and/or folded when deflated and unfurls when pressurised by the cooling fluid. The inflatable member may, for example, be compactly folded before use of the ablation probe to provide a compact insertion configuration. A folded portion of the inflatable member may be stored within a channel (e.g. in the tube 226) to minimise the insertion profile of the ablation probe 200 when in the insertion configuration. The use of a non-compliant material may allow an inflatable member with a larger deployed size, or stepped/tapered profile as will be described later. The inflatable member may be adapted to optimise the wall thickness and minimise the overall profile of the ablation probe. For example, the inflatable member may be manufactured by blow moulding a preform to give the desired shape. The preform may be shaped such that a thin walled inflatable member is produced once it has been blown into the mould. For example, the preform may be shaped, e.g. by grinding, to control the wall thickness of the inflatable member once blown into the mould. This can be used to achieve low wall thickness in portions of the inflatable member where there is low stretch ratio, e.g. in the edges (e.g. sleeves) of the inflatable member. A vacuum may again be used to collapse the deformable member once ablation therapy is complete. When refolded using a vacuum the inflatable member may not return to the same neat folded configuration it started in before insertion, but may collapse sufficiently to allow removal of the ablation probe. An example of the non-compliant inflatable member moving from the deflated to the inflated configurations is shown schematically in FIGS. 13a and 13b. In yet other embodiments, the inflatable member may be formed from a mixture of compliant, semi-compliant and non-compliant materials.

The deformable member 110 may extend along at least part of the length of the needle portion 212 as shown in the Figures. The deformable member 110 may, for example, extend from at or near the boundary between the needle portion 212 and the catheter portion 214 and end at or near the proximal end of the applicator 202. The coolant may therefore flow through the deformable member 210 along the length of the ablation probe (e.g. a flow of coolant may be provided between an inlet and an outlet of the deformable member, the inlet and outlet being spaced apart along the length of the ablation probe). The deformable member 210 may be fluidly connected to the non-deformable coolant return conduit at a boundary between the needle portion 212 and the catheter portion 214. The coolant may therefore flow through the deformable member 110 (when in the deployed configuration) and then through the non-deformable coolant return conduit in the catheter portion to reach the proximal end of the ablation probe 200.

In some embodiments, the deformable member may terminate at or near the proximal end of the applicator 202. In such an embodiment, the distal end of the deformable member may be coupled to the tube 226, a proximal portion of the applicator 202, or a separate coupling member as previously described. In other embodiments, the deformable member 110 is arranged to at least partly surround the applicator 202 as shown in FIG. 14. In such an embodiment, the applicator 202 is therefore located at least partly within the deformable member 210 and is therefore surrounded by the cooling fluid. This may help to reduce charring effects in surrounding tissue during therapy delivery. In this embodiment, the cooling fluid may be water or a similar substance with a suitable electrical permittivity to effectively transfer of the microwave energy into the surrounding tissue.

The deformable member 210 may surround all of the circumference of the ablation probe 200 as shown FIG. 14 to form a coolant conduit around the tube 226 (and membrane 228 and/or applicator 202 respectively) when in the deployed configuration. In other embodiments, the deformable member 210 may surround only part of the tube 226 (and membrane 228 and/or applicator 202 respectively). In one embodiment, as shown in FIG. 15, the deformable member 210 comprises one or more elongate deformable channels 240 running along at least part of the length of the ablation probe 200. The one or more deformable channels 240 may comprise a plurality of channels equally spaced around a circumference of the ablation probe 200 as shown in FIG. 15. In the described embodiment, four equally spaced deformable channels may be provided. The deformable channels 240 may be arranged in between the channels 230 forming the coolant delivery path. In other embodiments, any or suitable arrangement, number, or geometry of channels may be provided.

In some embodiments, the deformable channels 240 may be linked by a portion or portions of the inflatable member which do not change shape when the inflatable member moves to the inflated configuration. These non-inflatable portions may be arranged to cover the channels 230 in the tube 226 to provide a boundary of the coolant delivery path. This may mean that the membrane is not required (e.g. it is replaced by a non-expanding portion(s) of the inflatable member). An example of this is shown in FIG. 16. In this embodiment, four deformable channels 240 are provided around the circumference of the ablation probe (shown in a deployed or inflated state in FIG. 16). The deformable channels 240 are interspersed by four channels 230 in the tube 226. In this embodiment, the channels 230 are equally spaced at 12 o'clock, 3 o'clock, 6 o'clock, and 9 o'clock positions, with the deformable channels 240 spaced equally between them. In other embodiments, the channels and deformable channels may have other numbers and arrangements and may not be equally spaced.

In some embodiments, the deformable member 210 may be arranged, when in the deployed configuration, to control any one or more of the shape, size and position of an ablation zone produced by the applicator 202. For example, the shape and position of the deformable member 210 when in the deployed configuration may be adapted to control the ablation zone. The deformable member 210 may be adapted to provide an advantageous ablation zone to efficiently heat the tissue which is to be treated, and to reduce the heating of other tissue. In some embodiments, the deformable member 210 in the second configuration is arranged to generate a generally spherical ablation zone. This may provide a uniform distribution of energy over the ablation zone and provide improved heating. In other embodiments, other shaped ablation zones may be generated by appropriate size, shape and positioning of the deformable member 210.

In some embodiments, when in the deployed configuration, the deformable member 210 may have a larger size at or near a proximal end of the applicator 202 to control the ablation zone. This may ensure a significant volume of the cooling fluid is positioned adjacent to the proximal end of the applicator 202 to provide a heat sink to control heating effects and, therefore, the shape of the ablation zone. In the described embodiment, the deformable member 210 forms any one of a non-uniform tapered, bulbous or conical shape when in the deployed configuration to control the ablation zone. An example of this can be seen in FIG. 17 where a large diameter section 210a of the deformable member 210 is provided to control the ablation zone.

In yet other embodiments, the deformable member 210 may be arranged such that movement to the deployed configuration causes flexing of the ablation probe 200 to direct the energy applied by the applicator 202. In this embodiment, the deformable member 210 may be arranged to direct the applicator 202 to deliver energy in a directed orientation. The deformable member may bias the bending of the ablation probe through the biasing of the deformable member position and/or its material properties. The inflation of the deformable member 210 may thus cause bending or flexure of the ablation probe 200 so as to direct the energy. This may be achieved by coupling the deformable member on one side of the ablation probe 200 (e.g. so it extends around only part of its circumference) such that inflation of the deformable member causes the surface to which it is coupled (or in between its proximal and distal bonding locations) to be axially placed in tension or compression, hence causing bending of the ablation probe 200. An example of this can be seen in FIGS. 18a and 18b. In FIG. 18a an off-axis deformable member is shown. When the off axis deformable member is deployed the ablation probe may flex as shown in FIG. 18b.

When in the deployed configuration, the deformable member 210 may be shaped to anchor the ablation probe relative to the surrounding tissue. The deformable member 210 may therefore act to provide a return path for coolant along as well as anchoring the ablation probe. This may avoid the need for a second anchoring means, which may reduce the size of the ablation probe 200. By anchoring the ablation probe 200, the deformable member 210 may act to combat undesirable movement of the applicator 202 during the ablation procedure. It may, for example, reduce movement due to the displacements associated with breathing. Moreover, the deformable member 210 profile when in the deployed configuration may be optimised (for example by adding a bulbous or tapered section) to further improve anchoring and as well as mitigating undesirable heating effects that influence the ablation zone as described above. The deformable member 210 may therefore provide a number of different functions (return flow of coolant and/or control of the ablation zone and/or anchoring) in a single structure. This may reduce the overall size of the ablation probe 200.

In other embodiments, additional anchoring may be provided through the use of a separate anchoring mechanism (not shown in the Figures). The anchoring mechanism may comprise a helical wire or hollow screw thread at the distal portion of the antenna. This helical wire may act to anchor the antenna 202 in position by rotating the ablation probe 200 such that the screw is anchored into the adjacent tissue. The helical screw anchor may be male or female in construction and may be located distal to or concentric with the distal tip of the antenna 202. The material used for the anchor may be selected to ensure it is compatible with the energy modality and applicator configuration. For example, a non-metallic material may be used if a microwave probe is used.

In some embodiments, the ablation probe 200 may comprise one or more sensors (labelled 241 in FIG. 16) arranged to sense whether the deformable member has moved into the deployed configuration. The sensor(s) may be arranged to sense one or more properties of the applicator 202 or the energy applied to the surrounding tissue to determine the configuration of the deformable member 210.

In some embodiments, the successful inflation of the deformable member 210 may be determined by monitoring the reflected power from the applicator, which is minimised only when the deformable member 210 is inflated. This may be used to provide feedback to the physician during therapy delivery. The deformable member 210 behaviour may also be determined by monitoring the pressure of the cooling fluid. For example, when the cooling fluid is pressurised, it can be inferred that the deformable member 210 is inflated and when a vacuum is applied it is deflated. Alternatively, the volume of the coolant may be used to determine the status of the deformable member, where the volume of cooling fluid delivered is used to determine if the deformable member has inflated correctly.

In yet other embodiments, the ablation probe 200 may comprise a sensor or series of sensors to monitor tissue properties to ensure correct placement of the device or track the progress of the ablation. For example, the sensor(s) may comprise temperature sensor(s) (e.g. thermocouples) or an electrical impedance sensor(s).

The sensor(s) may be provided at any suitable location in the ablation probe 200. For example, the sensor(s) may be provided within the deformable member 210 (e.g. may be within one of the deformable channels shown in FIG. 16). The geometry of the deformable member 210 may be optimised to facilitate the sensor placement and provide suitable feedback on the tissue properties and ablation process. For example, the sensor(s) may be positioned in the wall of the deformable member 210, or in the coolant return path formed by the deformable member 210. In other embodiments, the sensor(s) may be provided within the coolant return path or within the applicator 202.

In some embodiments, the ablation probe 200 may further comprise a separate choke element. The choke element may be disposed at the distal end of the applicator 202 so as to control the shape of the ablation zone. In some embodiments, the choke element may be formed at least partly from a flexible material so as not to impede the overall flexibility of the ablation probe. For example, the choke element may be formed from a mixture of a ceramic and a metallic material. In some embodiments, the choke element may be positioned such that it is cooled by the coolant flowing via the coolant delivery path to help keep the choke cool during use. The choke element may, for example, be integrated with the tube housing the feeding cable to provide a compact arrangement.

A schematic view of the choke element 242 is shown in FIG. 19. The choke element 242 may form a short circuited balun which is active at microwave frequencies. The choke element 242 may be integrated at the proximal end of the applicator 202 where it is attached to the tube 226 housing the feeding cable 204a.

The choke element 242 may be active when the ablation probe 200 operates with microwave ablation energy. The choke element 242 may provide a high impedance condition at or near the proximal end of the applicator 202 to minimise reflected power flowing along the conductor. In some embodiments, the choke element 242 may be formed by the insertion of the material forming the applicator between the tube 226 housing the feeding cable and the feeding cable. The applicator material may extend for a distance of about one-quarter wavelength from the distal end of the tube 226 housing the feeding cable along the outer conductor (e.g. the applicator material may overlap the outer conductor). The portion of the applicator extending into the tube 226 may have one or more applicator coolant channels (e.g. as shown in FIG. 9 and labelled 232) to allow coolant to flow through (e.g. to flow to the deformable member)

In some embodiments, the portion of the applicator material extending over the feeding cable 204 may be formed by one or more finger portions (two of which are shown in FIG. 19) extending from the proximal end of the applicator 202. In other embodiments, an electrical connection may be made between the outer conductor of the feeding cable 204 and the tube 226 housing the feeding cable at a distance of about one-quarter wavelength proximally from a distal end of the tube. In these embodiments, the term "wavelength" refers to the wavelength of electromagnetic energy corresponding to the operating frequency of the ablation probe. In some embodiments, the choke element 242 may be miniaturised so as not to impair the flexibility of the ablation probe 200. In yet further embodiments, the choke element 242 may be cooled by the coolant delivery or return path to mitigate over heating during the treatment process.

Another example of the choke element 242 is shown in FIG. 20. The choke is formed by the (electrically conducting) tube housing the feeding cable, an outer conductor of the feeding cable and an electrically conducting coating at a proximal end of an applicator of the ablation probe. In this example, the applicator material again extends into tube 226 housing the feeding cable. The portion of the applicator material extending into the tube 226 may comprise a metallic coating 243 (e.g. a metallic paste or other suitable metallic deposition formed on the applicator) arranged to provide an electrical connection between the outer conductor of the feeding cable and the tube housing the feeding cable. The metallic coated portion of the applicator material may form a base of the choke by being applied to the proximal end face of the applicator material extending into the tube 226.

As discussed above, the ablation probe of any embodiment described herein may comprise a connector arranged to mechanically and electrically splice a distal portion of a feeding cable to the proximal portion of a feeding cable. An example of such a connector 300 is shown in FIG. 21. FIG. 21 shows a feeding cable having a distal portion 304a connected to a proximal portion 304b. The distal portion 304a comprises an inner conductor 306a, an outer conductor 308a, and a dielectric material 310a between them. The proximal portion 304b comprises an inner conductor 306b, an outer conductor 308b, and a dielectric material 310b between them.

The connector 300 comprises a joining member 312 arranged to mechanically and electrically couple the distal portion 304a of the feeding cable to the proximal portion 304b of the feeding cable. The joining member 312 comprises a proximal end 312b shaped to receive an end of the proximal portion 304b of the feeding cable and a distal end 312a shaped to receive an end of the distal portion 304a of the feeding cable. This may allow a compact and secure mechanical and electrical connection to be formed between the portions of the feeding cable. The joining member may provide a short connector between the portions of the feeding cable. This may improve the flexibility of the ablation probe so that it can be inserted through a working channel.

The inner conductors 306a, 306b of each portion of the feeding cable may be electrically coupled within the body of the connector 300 by soldering or any other suitable method.

As described in connection with other embodiments above, the ablation probe may comprise a tube 336 arranged to house the distal portion 304a of the feeding cable. A portion of the connector 300 may be arranged to extend within the tube 336 to form a mechanical coupling between them. As can be seen in FIG. 21, the joining member 312 may comprise a step portion 314 arranged to extend within the tube 336 to provide a mechanical coupling between the joining member 312 and the tube 336. This may reinforce the joint between the portions of the feeding cable. The step portion 314 may further act to space apart the tube 336 and the distal portion 304a of the feeding cable.

The connector 300 may further comprise a dielectric member 316, wherein the dielectric member is arranged to at least partly fill a region between an inner conductor of the proximal and/or distal portion of the feeding cable and the respective outer conductor of the proximal and/or distal portion of the feeding cable. The dielectric member 316 may fill all of the region between the inner conductor of the distal portion, the inner conductor of the proximal portion, the outer conductor of the distal portion and the outer conductor of the proximal portion. In the described embodiment, the dielectric member 316 completely fills the region between the inner conductor 306a and outer conductor 308a of the distal portion 304a. In other embodiments, only part of this region may be filled by the dielectric member 316. In yet other embodiments, the region between the inner and outer conductors (of either or both the distal and proximal feeding cable portions) may be filled with air rather than the dielectric member 316.

The connector 300 further comprises a sealing member 318. The sealing member is arranged to at least partially surround a connection region between the connector and either of the distal portion and proximal portions 304a, 304b of the feeding cable. As can be seen in FIG. 21, the sealing member may comprise a sealing layer disposed over the joining member 312 and one or both of the proximal portion and distal portion of the feeding cable to seal the connection between them.

Another example of an ablation probe 400 according to the present disclosure is shown in FIGS. 22a and 22b. Reference numerals corresponding to those used in FIGS. 1a and 1b have been used in FIGS. 22a and 22b for ease of understanding.

In the previously described embodiments, only one of the fluid return path and the fluid delivery path are provided by the deformable member. FIGS. 22a and 22b show an ablation probe 400 comprising a first deformable member 410a and a second deformable member 410b. Both the first deformable member 410a and the second deformable member 410b are arranged to move between an insertion configuration in which insertion of the probe is facilitated and a deployed configuration. Similarly to the embodiment of FIGS. 1a and 1b, a coolant return path 408 is provided by the second deformable 410b member when in the deployed configuration (the second deformable member 410b thus corresponds to the single deformable member 110, 210 of the embodiments previously described). A coolant delivery path 406 is provided at least partly by the first deformable member 410a. This may allow the cross sectional size of the ablation probe to be further reduced when the deformable members 410a, 410b are in the insertion configuration, whilst still allowing adequate flow of coolant when they are in deployed configuration.

The first deformable member 410a may have features corresponding to those of the deformable member 110, 210 described in relation to the other embodiments already introduced. The first deformable member 410a may at least partly surround a tube 426 housing the distal portion of the feeding cable 404. It may additional or alternatively surround at least part of the applicator 402.

In the embodiment shown in FIGS. 22a and 22b, the coolant delivery path is formed by both a conduit formed between the distal portion of the feeding cable 404 and the tube 426 which houses it and a conduit formed between the tube 426 and the first deformable member 410a. Both a deformable and non-deformable conduit may therefore be provided for the coolant delivery path to aid coolant flow. In other embodiments, the coolant delivery path may be provided only by a conduit formed between the first deformable member and the tube (i.e. there may be no coolant flow within the tube).

FIGS. 22a and 22b show the coolant delivery path being provided by the first deformable member 410a and the coolant return path being formed by the second deformable member 410b. In other embodiments, the flow of coolant may be reversed. Optionally, first deformable member (410a) may be constructed from a heat resistant material (for example, a thermoset, PTFE or polyamide).

In some embodiments, the ablation probe of any embodiment described herein may comprise a sheath member 504 as shown in FIGS. 23a and 23b. In this embodiment, the needle portion comprises a pointed tip 501 adapted to pierce tissue during use. The pointed tip may be provided on the distal tip of the applicator 502 as shown in the figures, but may be provided on any other component forming the distal tip of the ablation probe.

The sheath member 504 may be movable between a first position (shown in FIG. 23a) in which it surrounds the pointed tip and a second position (shown in FIG. 23b) in which the pointed tip is uncovered. The sheath member 504 may move between the first and second position as the pointed tip 501 of the ablation probe is inserted into tissue 506 during use. The pointed tip 501 of the ablation probe may therefore be covered by the sheath member 504 while it is inside the working channel 508 through which the ablation probe is inserted. This may reduce the risk of damaging the working channel 508 when inserting the ablation probe. Movement of the ablation probe into tissue may cause the sheath member 504 to move in a proximal direction along the length of the ablation probe from the first to the second position.

Another embodiment in which the distal tip of the ablation probe may be covered for insertion into a working channel is shown in FIGS. 24a, 24b and 24c. These Figures show an ablation probe 600 comprising an applicator 602 having a distal tip 634, a feeding cable 604, a deformable member 610 and a tube 626 housing the distal portion of the feeding cable. These components may correspond to those of the other embodiments described herein. The ablation probe 600 is inserted into a working channel 608.

A catheter coolant conduit forming part of the coolant return path in addition to that within the deformable member 610 is also provided. The catheter coolant conduit may be formed from a catheter tube 622 (e.g. corresponding to coolant return tube 222) surrounding the feeding cable 604. The catheter coolant conduit may be fluidly coupled to the deformable member 610 so that coolant can flow between them. For example, as shown in FIGS. 24*a*, 24*b*, 24*c* the deformable member 610 may be coupled proximally to the catheter tube 622 and distally to the applicator 602 (or to the tube 626 housing the feeding cable 604) to form a conduit for the cooling fluid.

The applicator 602, the tube 622 housing the distal portion of the feeding cable and the feeding cable 604 may be movable relative to the catheter tube 622. They may be moveable between a sheathed configuration (shown in FIG. 24*a*) in which the distal tip 634 of the applicator 602 is surrounded by the deformable member 610 and an unsheathed configuration (shown in FIG. 24*b*) in which the distal tip 634 of the applicator 602 is not surrounded by the deformable member 610. The combined assembly formed by the applicator 602, feeding cable housing tube 626 and the feeding cable 604 (e.g. both a distal and a proximal portion together) may move relative to the catheter tube 622 axially in a direction along the length of the ablation probe as shown in the figures.

The applicator 602 may therefore be located within the deformable member 610 such that the distal tip 634 (which may have a pointed tip to pierce tissue) is sheathed within the deformable member 610 to facilitate delivery through the working channel 608. This may reduce the risk of the tip of the applicator 602 damaging the inside wall of the working channel 608, especially wherein the working channel follows a tortuous path. When required, the applicator 602 may be moved from the sheathed to the unsheathed configuration so that it is extended from within the deformable member.

When in the unsheathed configuration the deformable member 610 (or at least part of it) may be folded or wrapped as shown in FIG. 24*a*. The deformable member 610 may be unfolded by movement to the unsheathed configuration shown in FIG. 24*b*. Once in the unsheathed configuration, the deformable member 610 may be moved from the insertion configuration (shown in FIG. 24*b*) to the deployed configuration (shown in FIG. 24*c*) as described above in relation to other embodiments.

In another embodiment, the distal tip 634 of the applicator 602 may be surrounded by the catheter tube 622 when in the sheathed configuration. An example of this is shown in FIGS. 25*a* and 25*b*. FIG. 25*a* shows a sheathed configuration in which the applicator 602, the tube 626 housing the distal portion of the feeding cable 604 and the feeding cable 604 have been moved relative to the catheter tube 622 into a sheathed configuration in which the distal tip 634 of the applicator is surrounded by the catheter tube. FIG. 25*b* shows an unsheathed configuration in which the applicator 602, the tube 626 housing the distal portion of the feeding cable 604 and the feeding cable 604 have been moved relative to the catheter tube 622 so that the distal tip 634 of the applicator is not surrounded by the catheter tube and can be inserted into tissue.

Various modifications will be apparent to the skilled person without departing form the scope of the claims.

The work leading to this invention has received funding from the European Research Council under the European Union's Horizon-2020 Programme (H2020)/ERC grant agreement no 637780.

The invention claimed is:

1. An ablation probe comprising:
an applicator arranged to apply radiation to heat surrounding tissue;
a feeding cable arranged to supply electromagnetic energy to the applicator, the feeding cable comprising a coaxial cable comprising a distal portion and a proximal portion, each having an inner conductor and an outer conductor arranged to shield the inner conductor;
a first coolant flow path via which coolant is able to flow;
a deformable member arranged to move between an insertion configuration in which insertion of the probe is facilitated and a deployed configuration, wherein the deformable member comprises a non-compliant material arranged to fold or unfold in order to move between the insertion and deployed configurations;
a second coolant path, via which coolant is able to flow, the second coolant path being provided by the deformable member when in the deployed configuration, wherein the deformable member and the second coolant path have a cross-sectional size defined in a plane normal to a longitudinal axis of the ablation probe, and the cross-sectional size of the deformable member is greater in the deployed configuration compared to the insertion configuration whereby the second coolant path is formed, or is increased in cross sectional-size, by movement of the deformable member from the insertion configuration to the deployed configuration, wherein a combination of the first and second coolant paths form a coolant circuit arranged to deliver a flow of coolant towards and away from the applicator, wherein coolant is able to flow: towards the applicator via the first coolant path and away from the applicator via the second coolant path; or away from the applicator via the first coolant path and towards the applicator via the second coolant path; and
a tube arranged to house the distal portion of the feeding cable, wherein the deformable member surrounds at least part of the tube, wherein the ablation probe comprises:
 a. a needle portion adapted to be inserted into tissue during use, the needle portion comprising: the deformable member; the applicator; the distal portion of the feeding cable; at least part of the tube housing the distal portion of the feeding cable; and a distal portion of the first coolant path, wherein the distal portion of the first coolant path is located outside of the feeding cable such that it extends at least partly around the outer conductor of the distal portion of the feeding cable, and
 b. a catheter portion comprising: a proximal portion of the feeding cable; a proximal portion of the first coolant path; and a non-deformable coolant conduit, wherein the deformable member is fluidly connected to the non-deformable coolant conduit at a boundary between the needle portion and the catheter portion.

2. An ablation probe according to claim 1, wherein the distal portion of the feeding cable has a distal cross sectional size, and the proximal portion of the feeding cable has a proximal cross sectional size, wherein the distal cross sectional size is less than the proximal cross sectional size.

3. An ablation probe according to claim 1, wherein either or both of:
the tube is formed from a superelastic material; or
the tube is formed from an electrically conductive material.

4. An ablation probe according to claim 1, wherein any one or more of:
   a) the second coolant path is provided only by the deformable member along at least a portion of a length of the probe;
   b) the deformable member is fluidly connected to a distal end of the first coolant path; or
   c) a greatest cross sectional size of the needle portion is less than a greatest cross sectional size of the catheter portion.

5. An ablation probe according to claim 2, further comprising a connector arranged to mechanically and electrically splice the distal portion of the feeding cable to the proximal portion of the feeding cable.

6. An ablation probe according to claim 5, wherein any one or more of:
   a) the connector comprises a joining member arranged to mechanically and electrically couple the distal portion of the feeding cable to the proximal portion of the feeding cable, wherein the joining member comprises a proximal end shaped to receive the proximal portion of the feeding cable and a distal end shaped to receive the distal portion of the feeding cable;
   b) a portion of the connector is arranged to extend within the tube housing the distal portion of the feeding cable to form a mechanical coupling between them;
   c) the connector comprises a dielectric member, wherein the dielectric member is arranged to at least partly fill a region between the inner conductor of the proximal and/or distal portion of the feeding cable and the respective outer conductor of the proximal and/or distal portion of the feeding cable; and
   d) the connector comprises a sealing member, sealing member at least partially surrounding a connection region between the connector and either or both of the distal portion of the feeding cable and the proximal portion of the feeding cable.

7. An ablation probe according to claim 1, wherein the catheter coolant conduit is formed from a catheter tube coupled to the deformable member, and wherein the applicator, the tube housing the distal portion of the feeding cable and the feeding cable are movable relative to the catheter tube between a sheathed configuration in which a distal tip of the applicator is surrounded by the deformable member and an unsheathed position in which the distal tip of the applicator is not surrounded by the deformable member, and optionally:
   wherein in the sheathed configuration the applicator distal tip is located within the catheter tube wherein in the unsheathed configuration the distal tip of the applicator is not located within the catheter tube and the deformable member remains connected to both a distal section of the catheter tube and the applicator.

8. An ablation probe according to claim 1, wherein one or both of:
   a) the deformable member is arranged to at least partly surround the applicator in the deployed configuration; or b) when in the deployed configuration, the deformable member is shaped to anchor the ablation probe relative to the surrounding tissue.

9. An ablation probe according to claim 1, further comprising a bridging member arranged to couple the applicator to the tube housing the distal portion of the feeding cable, wherein the bridging member comprises a bridging tube surrounding a part of the tube and a part of the applicator so that it bridges the connection between them.

10. An ablation probe according to claim 1, wherein (a) the deformable member comprises one or more elongate deformable channels running along the length of the ablation probe, or (b) the deformable member comprises a plurality of deformable channels running along the length of the ablation probe and wherein the deformable channels are equally spaced around a circumference of the ablation probe.

11. An ablation probe according to claim 1, wherein the ablation probe further comprises a coupling member, the coupling member arranged to couple the deformable member to the applicator, wherein any one or more of:
   a) the coupling member is formed from a material different from the applicator, wherein the coupling member is arranged to form a bonding site to which the deformable member is bonded;
   b) the coupling member is shaped to form a mechanical coupling with the applicator, and wherein the coupling member is formed from a coupling tube surrounding the applicator, the coupling tube having a close fit with an outer surface of the applicator to form a friction fit between them; and
   c) the coupling member is formed from an electrically insulating material.

12. An ablation probe according to claim 1, wherein any one or more of:
   a) the first coolant path comprises a coolant channel formed between an inside surface of the tube surrounding the feeding cable and an outside surface of the feeding cable;
   b) the first coolant path comprises one or more coolant channels formed in the body of the tube housing the feeding cable; and
   c) the first coolant path comprises one or more coolant channels formed in the outer conductor.

13. An ablation probe according to claim 12, wherein the one or more coolant channels comprise one or more slots in an outer surface of the tube or an outer surface of the outer conductor, and wherein the ablation probe further comprises a membrane disposed around the tube or the outer conductor, the membrane arranged to separate the first coolant path and from the second coolant path, and/or
   wherein the one or more coolant channels are disposed along a length of the outer conductor or the tube; and/or
   wherein the one or more coolant channels comprise a plurality of channels spaced equally around a circumference of the outer conductor or the tube.

14. An ablation probe according to claim 1, wherein the applicator further comprises one or more applicator coolant channels fluidly connected to the first coolant path, and at least one of:
   wherein the one or more applicator coolant channels are formed by one or more recesses in an outer surface of the body of the applicator; and
   wherein the deformable member at least partly surrounds the applicator, and wherein the ablation probe further comprises an insulating member disposed between the deformable member and the applicator.

15. An ablation probe according to claim 14, wherein the applicator comprises an insertion region arranged to extend into the tube housing the distal portion of the feeding cable, the insertion region comprising one or more channels arranged to fluidly couple the first coolant path to the applicator coolant channels.

16. An ablation probe according to claim 1, further comprising a sensor arranged to sense whether the deformable member has moved into the deployed configuration, wherein the sensor is arranged to sense one or more properties of the applicator or the energy applied to the surrounding tissue to determine the configuration of the deformable member.

17. An ablation probe according to claim 1, wherein the probe further comprises a choke element disposed at a proximal end of the applicator, and any one or more of:
a) wherein the choke element is formed at least partly from a flexible material;
b) wherein the choke element is cooled by the coolant flowing via the first coolant path;
c) wherein the choke element is integrated with the tube housing the feeding cable;
d) wherein the choke element comprises a portion of the applicator extending between the outer conductor of the feeding cable and the tube housing the feeding cable.

18. An ablation probe according to claim 1, wherein the deformable member is a second deformable member, the ablation probe further comprising a first deformable member arranged to move between an insertion configuration in which insertion of the probe is facilitated and a deployed configuration, wherein the first coolant path is provided at least partly by the first deformable member when in the deployed configuration.

19. An ablation probe according to claim 1, wherein the ablation probe is suitable for insertion through the working channel of an intraluminal delivery device.

\* \* \* \* \*